United States Patent
Mutz et al.

(10) Patent No.: US 7,270,986 B2
(45) Date of Patent: *Sep. 18, 2007

(54) EJECTION OF LOCALIZED VOLUMES FROM FLUIDS

(75) Inventors: Mitchell W. Mutz, Palo Alto, CA (US); Richard N. Ellson, Palo Alto, CA (US); David Soong-Hua Lee, Mountain View, CA (US)

(73) Assignee: Picoliter Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/049,206

(22) Filed: Feb. 1, 2005

(65) Prior Publication Data

US 2005/0130257 A1    Jun. 16, 2005

Related U.S. Application Data

(63) Continuation of application No. 10/040,926, filed on Dec. 28, 2001, now Pat. No. 6,849,423, which is a continuation-in-part of application No. 09/751,666, filed on Dec. 28, 2000, now abandoned, which is a continuation-in-part of application No. 09/727,391, filed on Nov. 29, 2000, now abandoned.

(51) Int. Cl.
*C12N 13/00* (2006.01)

(52) U.S. Cl. ................................. 435/173.9; 435/29

(58) Field of Classification Search ................. 435/29, 435/173.1

See application file for complete search history.

(56) References Cited

U.S. PATENT DOCUMENTS 2,056,426 A    10/1936    Frantz (Continued)

FOREIGN PATENT DOCUMENTS

EP    0801305 A1    10/1997

(Continued)

OTHER PUBLICATIONS

U.S. Appl. No. 09/669,194, filed Sep. 25, 2000, Ellson et al.
U.S. Appl. No. 09/669,996, filed Sep. 25, 2000, Ellson et al.
U.S. Appl. No. 09/727,392, filed Nov. 29, 2000, Mutz et al.
U.S. Appl. No. 09/962,730, filed Sep. 25, 2001, Ellson et al.
U.S. Appl. No. 09/964,193, filed Sep. 25, 2001, Mutz et al.
U.S. Appl. No. 09/964,212, filed Sep. 25, 2001, Ellson et al.

(Continued)

*Primary Examiner*—Ralph Gitomer
(74) *Attorney, Agent, or Firm*—Dianne E. Reed; Mintz, Levin, Cohn, Ferris, Glovsky and Popeo, P.C.

(57) ABSTRACT

A method is provided for acoustically ejecting from a channel or other container a plurality of fluid droplets, each of which contains one or more particles or other localized volumes. The localized volumes, which can be living cells, are ejected towards sites on a substrate surface, a container, or a channel. An integrated cell sorting and arraying system is also provided that is capable of sorting based upon cellular properties by the selective ejection of cells from a carrier fluid. The cells can be ejected with adjustable velocity and trajectory. The ejected cells can be directed to form an array, wherein each site of the array can contain a single cell. Additionally provided is a method of forming arrays of single live cells more efficiently, rapidly, flexibly, and economically than by other cell array approaches. This method permits efficient, continuous, and simultaneous sorting of cells based upon the quantitative or semiquantitative measurement of cellular properties, and also permits non-binary or severally-branched decision-making. An integrated system, which includes a processor, and methods are also provided for the detection, selection, and ejection of selected particles or circumscribed volumes, such as live cells, from a continuous stream of fluid-suspended particles or other circumscribed volumes flowing in channels.

15 Claims, 12 Drawing Sheets

U.S. PATENT DOCUMENTS

| | | | |
|---|---|---|---|
| 3,380,584 A | 4/1968 | Fulwyler | |
| 3,710,933 A | 1/1973 | Fulwyler et al. | |
| 4,308,547 A | 12/1981 | Lovelady et al. | |
| 4,500,707 A | 2/1985 | Caruthers et al. | |
| 4,743,361 A * | 5/1988 | Schram | 209/1 |
| 4,765,737 A | 8/1988 | Harris et al. | |
| 4,877,516 A * | 10/1989 | Schram | 209/155 |
| 5,041,849 A | 8/1991 | Quate et al. | |
| 5,158,889 A | 10/1992 | Hirako et al. | |
| 5,436,327 A | 7/1995 | Southern et al. | |
| 5,506,141 A | 4/1996 | Weinreb et al. | |
| 5,700,637 A | 12/1997 | Southern et al. | |
| 5,798,779 A | 8/1998 | Nakayasu et al. | |
| 6,044,981 A | 4/2000 | Chu et al. | |
| 6,103,479 A | 8/2000 | Taylor | |
| 6,120,735 A | 9/2000 | Zborowski et al. | |
| 6,416,164 B1 * | 7/2002 | Stearns et al. | 347/46 |
| 6,467,877 B2 | 10/2002 | Ellson | |
| 6,548,308 B2 * | 4/2003 | Ellson et al. | 436/180 |
| 6,596,239 B2 | 7/2003 | Williams et al. | |
| 6,603,118 B2 | 8/2003 | Ellson et al. | |
| 6,610,223 B2 | 8/2003 | Lee | |
| 6,612,686 B2 * | 9/2003 | Mutz et al. | 347/46 |
| 6,642,061 B2 * | 11/2003 | Ellson et al. | 436/180 |
| 6,666,541 B2 * | 12/2003 | Ellson et al. | 347/46 |
| 6,802,593 B2 * | 10/2004 | Ellson et al. | 347/46 |
| 6,809,315 B2 * | 10/2004 | Ellson et al. | 250/288 |
| 6,849,423 B2 * | 2/2005 | Mutz et al. | 435/29 |
| 6,855,925 B2 * | 2/2005 | Ellson et al. | 250/288 |
| 6,893,836 B2 * | 5/2005 | Mutz et al. | 435/29 |
| 6,938,987 B2 * | 9/2005 | Ellson et al. | 347/46 |
| 6,991,917 B2 * | 1/2006 | Mutz et al. | 435/29 |
| 2002/0037527 A1 | 3/2002 | Ellson et al. | |
| 2002/0094582 A1 * | 7/2002 | Williams et al. | 436/180 |

FOREIGN PATENT DOCUMENTS

| | | |
|---|---|---|
| EP | 0845357 A2 | 6/1998 |
| WO | WO92/18608 | 10/1992 |
| WO | WO94/27142 | 11/1994 |
| WO | WO97/45730 | 12/1997 |
| WO | WO 02/24324 | 3/2002 |

OTHER PUBLICATIONS

U.S. Appl. No. 09/999,166, filed Nov. 29, 2001, Mutz et al.

"CellSelector™" product description, Cell Robotics Inc., Albuquerque, NM, no date given.

Amemiya et al. (1997), "Ink Jet Printing with Focused Ultrasonic Beams," *IS&T NIP 13: 1997 International Conference on Digital Printing Technologies*, pp. 698-702.

Kotecha et al. (1996), "Increase in Interleukin (IL)-1β and IL-6 in Bronchoalveolar Lavage Fluid Obtained from Infants with Chronic Lung Disease of Prematurity," *Pediatric Research 40*(2):250-256.

Steel et al. (2000), "The Flow-Thru Chip™: A Three-Dimensional Biochip Platform," *Microarray Biochip Technology*, Chapter 5, pp. 87-117, BioTechniques Books, Natick, MA.

Theriault et al. (1999), "Application of Ink-Jet Printing Technology to the Manufacture of Molecular Arrays," DNA Microarrays: A Practical Approach, Ed. M. Schena, Chapter 6 (Oxford University Press).

O'Donnell-Maloney et al. (1996), "Microfabrication and Array Technologies for DNA Sequencing and Diagnostics," *Genetics Analysis Biomolecular Engineering 13*:151-157.

* cited by examiner

EJECTION OF LOCALIZED VOLUMES FROM FLUIDS

CROSS-REFERENCE TO RELATED APPLICATIONS

This application is a continuation of U.S. patent application Ser. No. 10/040,926, filed on Dec. 28, 2001, now U.S. Pat. No. 6,849,423, which is a continuation-in-part of U.S. patent application Ser. No. 09/751,666, filed Dec. 28, 2000, now abandoned, which is a continuation-in-part of U.S. patent application Ser. No. 09/727,391, filed Nov. 29, 2000, now abandoned, all of which are incorporated herein in their entireties by reference.

TECHNICAL FIELD

This invention relates generally to the use of focused acoustic energy in the spatially directed ejection of cells that are suspended in a carrier fluid. The methods and devices of the invention provide for efficient, non-destructive, and complete sorting of cells.

BACKGROUND

Methods for the efficient, non-destructive, and complete sorting of cells have widespread applications in basic biological and medical research. For example, cell sorting is commonly used in immunology, where cells displaying specific markers are segregated from other cells via an optical property such as fluorescence. Another application is in medical therapeutics, where a certain autologous or heterologous cell type is commonly desired for transplantation, as in therapy for neoplasia. Advances in the microfabrication of biocompatible materials, and of bioengineering in general, suggest that more effective cell sorting methods will also find use in tissue engineering applications.

Early cell sorting devices distinguished among cells based upon physical parameters. Such cell sorting techniques included filtration, which selects based on cell size, and centrifugation, which selects based on cell density. These methods are effective if the cell population of interest differs significantly in size or density from the other cells in a cell mixture. When the individual cell populations in the cell mixture are similar to each other in size and density, however, neither filtration nor centrifugation techniques can separate them effectively.

To overcome these disadvantages, techniques have been developed to distinguish and separate cell populations based on the display of surface markers or epitopes. These techniques differentiate between cell populations based on tagging elements attached to the cell surface, and have become significant cell-sorting tools. Fluorescence-activated cell sorting (FACS) employs a fluorescent antibody label or tag that binds a specific cell surface marker. Most such sorters operate primarily in a binary manner: selection is based solely upon whether or not a cell bears sufficient fluorescent labels to trigger separation based upon a preselected threshold fluorescence value. Because FACS sorters examine a single cell at a time, the rate of cell separation is relatively slow. Generally, a FACS sorter can provide a cell sorting rate of $10^3$ cells/second. Higher cell sorting rates are possible, but they may damage some cells. A limited number of FACS sorters are present in laboratories because they are costly and must be operated by skilled technicians.

Another separation method that utilizes cell tagging is known as high gradient magnetic separation (HGMS). Magnetic based sorting was first employed in the mining industry, and relies on differences in the intrinsic magnetic properties of the sorted materials for its operation (see U.S. Pat. No. 2,056,426 to Frantz). In HGMS, a heterogeneous cell population or cell mixture, which includes a magnetically tagged cell subpopulation, passes through an applied magnetic field, and the cells of the subpopulation labeled with magnetic tags are selectively attracted towards the magnetic source. The magnetically tagged subpopulation is collected by adherence to the magnetic source, or to a cell collector near the magnetic source. One shortcoming of HGMS, which can be faster than FACS, is that the cell subpopulation of interest can be damaged during the HGMS process due to massing of cells at the collector. HGMS is again primarily binary in nature, as separation is based solely on the presence or absence of magnetic tags.

Binary separation techniques based on a parameter such as magnetism or fluorescence have found considerable use in cell sorting. A need exists, however, for separating cells in a non-binary manner, based on the intensity of a specified parameter, such as the intensity of a detected magnetic or fluorescent signal.

Recently a system and method for sorting cells based on the quantity of magnetic tags bound to the cell has been described (U.S. Pat. No. 6,120,735 to Zborowski et al.), which uses a channel in which the tagged cells flow through a magnetic field. The method is capable of higher throughput, while maintaining comparable to higher cell viability, relative to traditional FACS or HGMS. A population of particles having different magnetic susceptibilities is subjected to a magnetic field during flow to create a gradient in the flow stream. Divided flow compartments within the channel are used to generate fractionated efferent flow streams. The particles in these fractionated cell flow streams are not, however, strictly sorted, but rather are enriched in particular fractions. Thus the higher throughput of fractionated enrichment methods, while maintaining cell viability, is obtained by a sacrifice in purity. A need therefore exists for methods of cell sorting that allow high throughput, with the flexibility to perform non-binary separations, without sacrificing purity.

Another recently described method for sorting cells provides high throughput and avoids mere enrichment, but sacrifices cells by destroying all detected unwanted cells with a laser (U.S. Pat. No. 5,158,889 to Hirako et al., 1992).

Some cell sorting methods include the ability to separate a single file, continuous procession of fluid-suspended cells in a channel into a procession of individual droplets containing single cells, as described in U.S. Pat. No. 3,710,933 to Fulwyler et al. and U.S. Pat. Nos. 3,380,584 and 4,148,718 to Fulwyler. The procession of individual droplets is created by vibrating a flow chamber or orifice through which the flow passes, usually at a frequency on the order of 40,000 Hz. These droplets, each containing a single cell, may be ejected from an orifice. In this method, the single-file cells are separated from each other by a significant distance, resulting in a smaller number of cells passing a detection or ejection point per unit of time relative to the number in a method that employs a continuous progression of single-file, nearly adjacent cells. Thus, sorting throughput and efficiency are relatively low, because selected cells cannot be ejected from the procession as rapidly as in the case where the fluid is continuous. Also, there is much inflexibility and inefficiency associated with the manipulating of individual cells in a channel containing many cells. The speed of manipulating individual cells in a channel is inherently limited, for example, because the flow may need to be slowed or stopped to prevent cellular collisions in a channel or system of interconnected channels.

An example of such a fluid-suspended cell sorter is the jet-in-air sorter, which is commonly optimized for commercial mammalian cell sorting. Lymphoid cells having diameters ranging from 8 to 14 µm, and spermatocytes having a long dimension of up to 200 µm, are commonly sorted by such a device. Jet-in-air systems that are piezo-based must be tuned to the specific diameters of the cells to be sorted, so that it is difficult to sort subpopulations of cells having substantially different mean sizes. Tuning such a system to accommodate different cell sizes or fluid viscosities involves adjusting parameters such as flow tip diameter, sheath pressure, flow rate, droplet drive frequency, drive amplitude, droplet spacing, and droplet breakoff point.

Piezo-based systems also tend to be inefficient for other reasons, including their need to space out cells in the flow stream to prevent cell bunching, which reduces the capacity to quickly locate cells for sorting operations. For example, to avoid cell bunching, one fluid droplet out of ten may contain a cell. Consequently, for a flow rate of 32,000 drops per second, only 3,200 cells per second would be counted, a 10-fold lower efficiency compared to the use of a system wherein each droplet contains a cell.

A need therefore exists for a method and system capable of sorting a large range of particle sizes that do not require the flow tip to be changed or other fluidic parameters to be adjusted. Indeed, a need exists for cell sorting methods and systems that do not use flow tips, to eliminate the potential for clogging. A need also exists for a sorting system and method that can readily discriminate between clumps of cells and single cells without clogging, permitting clumps to be identified and sorted separately. There is an additional need for a sorting system and method that can be adjusted to accommodate solutions of varying viscosities by merely changing the frequency and power settings on the energy transducer. A further need exists for a cell sorting system that can economically attain throughput and efficiency levels superior to those of current systems by, for example, the use of massively parallel, multi-channel sorting. Fundamental needs still exist for improved methods to differentiate cells according to multiple parameters, and to separate cells into two or more groups based on the degree of a single parameter (non-binary decision making), without sacrificing separation purity or cell viability.

For research purposes, numerous improvements are desired for cell sorting systems. Overall, there is a need for greater efficiency so that, for example, the total time is shortened between obtaining a cell mixture (for example a blood sample) and using the separated cells experimentally. Furthermore, experiments commonly require the plating of small numbers of a specific cell type onto individual plates, dishes, wells, or arrays thereof. Because all known cell sorting methods first collect all cells of a given subpopulation into one place, rather than permitting removal of individual selected cells directly into well plate wells or other containers, more steps are required between collecting a sample and having the collected cells ready for experimentation. Considerable laboratory time and effort can be saved by direct delivery of a precisely known small number of individually selected cells into containers for use in experiments, rather than collecting the entire separated subpopulation into a single container and then subdividing the cells into experimental vessels. Thus a need exists for employing a means for the non-binary selective removal of viable cells from a mixture of cells directly into an experimental vessel. This need can be met through the use of acoustic ejection.

There is no method or system currently known for sorting cells in which individual viable cells are ejected from a fluid. Thus a need exists for a method and corresponding system for sorting cells by ejecting viable single cells from a fluid, which preferably use non-binary selection and can deliver precise numbers of cells from a fluid directly into experimental containers. A method for ejecting single cells from a fluid is generally disclosed in copending U.S. patent applications Ser. Nos. 09/727,391 and 09/999,166, filed on Nov. 29, 2000 and Nov. 29, 2001, respectively, for "Focused Acoustic Energy for Ejecting Cells from a Fluid", inventors Mutz and Ellson, assigned to Picoliter Inc. (now Labcyte Inc. of Sunnyvale, Calif.). A method and system for cell sorting utilizing the acoustic ejection of individual selected cells contained in droplets offer increased flexibility and overall efficiency without reducing viability, as compared to existing methods, by virtue of their ability to deliver sorted cells directly into experimental containers and to sort cells into several, rather than just two, groups based on a single intrinsic or tagged property.

SUMMARY OF THE INVENTION

Accordingly, it is an object of the present invention to provide systems and methods that overcome the above-mentioned disadvantages of the prior art.

In one embodiment, a method is provided for separating localized volumes within a fluid, wherein each localized volume has a different acoustic impedance than the fluid. A detector is used to identify the location of one localized volume and determine one or more properties thereof. Then, focused energy, preferably focused acoustic energy, is applied to the fluid in a manner effective to eject the localized volume from the fluid as a droplet. A preferred ejection device is the acoustic ejection system described in U.S. patent applications Ser. Nos. 09/699,996 and 09/964,212 ("Acoustic Ejection of Fluids from a Plurality of Reservoirs"), inventors Ellson, Foote and Mutz, filed on Sep. 25, 2000 and Sep. 25, 2001, respectively, and assigned to Picoliter Inc. (now Labcyte Inc. of Sunnyvale, Calif.).

As described in the aforementioned patent application, the device enables acoustic ejection of a plurality of fluid droplets toward designated sites on a substrate surface for deposition thereon. Such devices comprise: a plurality of containers or reservoirs each adapted to contain a fluid capable of carrying, for example, cells or other localized volumes suspended therein; an acoustic ejector for generating acoustic radiation and a focusing means for focusing it at a focal point near the fluid surface in each of the reservoirs; and a means for positioning the ejector in acoustic coupling relationship to each of the containers or reservoirs. Preferably, each of the containers is removable, or comprised of an individual well in a well plate, and/or arranged in an array. In addition, the containers or reservoirs are preferably substantially acoustically indistinguishable from one another and have appropriate acoustic impedance and attenuation to allow the energetically efficient focusing of acoustic energy near the surface of a contained fluid.

In variations on the aforementioned method, the localized volumes are present in a flowing stream within a fluidic ejection channel on a substrate surface, or are living cells within a cell colony growing on a medium (typically agar or a similar semisolid or gel).

In another embodiment, a system is provided that employs focused acoustic ejection technology to selectively sort cells or other circumscribed volumes into channels or other containers that are substantially transected by a plane parallel to a surface of the fluid. This plane also transects the container from which droplets are ejected. Individual cells or other circumscribed volumes can be selected and then ejected at adjustable velocity onto a substantially planar substrate to form an array on the substrate. The operations of the system are performed by positioning an acoustic ejector so as to be in acoustically coupled relationship with a first reservoir that contains cells or other localized volumes in a first carrier fluid. After the presence of a localized volume sufficiently close to the fluid surface is acoustically detected, and any properties used as criteria for ejection are detected by acoustic and/or electromagnetic measurements, the ejector is activated to generate and direct acoustic radiation that has a focal point within, and near the surface of, the carrier fluid. The acoustic energy applied results in the ejection of a droplet of carrier fluid. When the system is used for cell ejection, the acoustic energy is applied in a manner effective to eject a droplet that is sufficiently small such that only a single cell may be contained therein. Preferably, the droplet is ejected with a velocity vector having a component parallel to the plane of the fluid surface. If desired, the ejector may be repositioned so as to be in acoustically coupled relationship with a second reservoir, and the process is repeated as above to eject a droplet of the second fluid. The system may also be configured so as to enable repetition with a plurality of fluid containers.

In a further embodiment, the invention provides a method of forming arrays of single living cells more efficiently, rapidly, flexibly, and economically than by other cell array forming approaches. The method permits the efficient, continuous, and simultaneous selection and sorting of cells based upon quantitative or semiquantitative measurements of their properties. The method also allows for the use of multiple ejection targets, non-binary cell selection, and severally-branched decision-making. The arrayed cells may be attached to the substrate surface by one or more specific binding systems, each employing an external marker moiety that specifically recognizes a cognate moiety, such as a ligand receptor pair. One such specific binding system uses streptavidin as an external marker moiety, generated by transformation, with biotin used as the cognate moiety. An example of a binding system that employs an endogenous external marker moiety (which exists without the need for cell transformation) uses externally displayed Ig lymphocyte clones and epitopes as the cognate moiety.

BRIEF DESCRIPTION OF THE DRAWINGS

FIG. 1 is not to scale, and certain dimensions may be exaggerated for clarity of presentation. FIG. 1A shows the acoustic ejector acoustically coupled to the first cell container or reservoir and activated in order to eject a droplet of fluid containing a single cell from within the first cell container or reservoir toward a designated site on a substrate surface. FIG. 1B shows the acoustic ejector acoustically coupled to a second cell container or reservoir.

FIG. 2A is a schematic top plane view of the two well plates, i.e., the cell container or reservoir well plate and the substrate surface having arrayed cells contained in fluid droplets. FIG. 2B illustrates in cross-sectional view a device comprising the cell container or reservoir well plate of FIG. 2A acoustically coupled to an acoustic ejector, wherein a cell contained in a droplet is ejected from a first well of the cell container or reservoir well plate into a first well of the substrate well plate. FIG. 2C illustrates in cross-sectional view the device illustrated in FIG. 2B, wherein the acoustic ejector is acoustically coupled to a second well of the cell container or reservoir well plate and further wherein the device is aligned to enable the acoustic ejector to eject a droplet from the second well of the cell container or reservoir well plate to a second well of the substrate well plate.

FIG. 3A illustrates the ejection of a cell-containing fluid droplet onto a designated site of a substrate surface. FIG. 3B illustrates the ejection of a droplet containing a first cell displaying a first marker moiety adapted for attachment to a modified substrate surface to which a first cognate moiety is attached. FIG. 3C illustrates the ejection of a droplet of second fluid containing a second cell displaying a second molecular moiety adapted for attachment to a different site on the surface. FIG. 3D illustrates the substrate and the first and second cells arrayed thereon by the process illustrated in FIGS. 3A, 3B and 3C.

FIG. 4A illustrates two different cells resident at adjacent array sites, contained in fluid droplets adhering to a designated site of a substrate surface by surface tension, with each cell further attached to the site by binding of streptavidin (SA) to a biotinylated (biotin (B) linked) surface. Streptavidin is displayed on the cell exterior as a result of transformation by a genetic coding sequence for external-display-targeted streptavidin. FIG. 4B illustrates two different cells resident at adjacent array sites, contained in fluid droplets adhering to a designated site of a substrate surface by surface tension, with each cell further attached to the site by binding of two externally displayed antigenic epitopes characteristic of the cell (here E1 and E2) to two different monoclonal antibodies (mAb-E1, mAb-E2) specific respectively for the different epitopes, each mAb linked to the surface at only one of the adjacent array sites.

FIGS. 5A and 5B illustrate the device schematically. FIG. 5C illustrates a top view of channels containing live cells, with the substrate surface having arrayed cells contained in fluid droplets. FIG. 5D illustrates a cross-section of a channel showing an upward protrusion of the channel floor to direct cells sufficiently close to the fluid surface for ejection. FIG. 5E illustrates a cross-section of a channel showing the use of focused energy, such as acoustic energy, to direct cells sufficiently close to the fluid surface for ejection.

FIG. 7A illustrates a side view of a vertical channel containing cells, within a larger vessel. Fluid from the vertical channel is only accessible to the periphery of the larger vessel by passing under an angled lip projecting laterally from the vertical channel, with the distance between the lip and the floor of the larger vessel decreasing radially outward so that cells can pass radially outwards from the central channel to the periphery. At the periphery, a channel is formed where cells are spaced further apart, relative to their spacing in the vertical channel. FIG. 7B is a top view showing cells along the side walls of the larger vessel; this configuration allows for the simultaneous ejection of a large number of cells by use of multiple ejectors, to effect a high throughput and efficiency.

DETAILED DESCRIPTION OF THE INVENTION

Figure 1A:
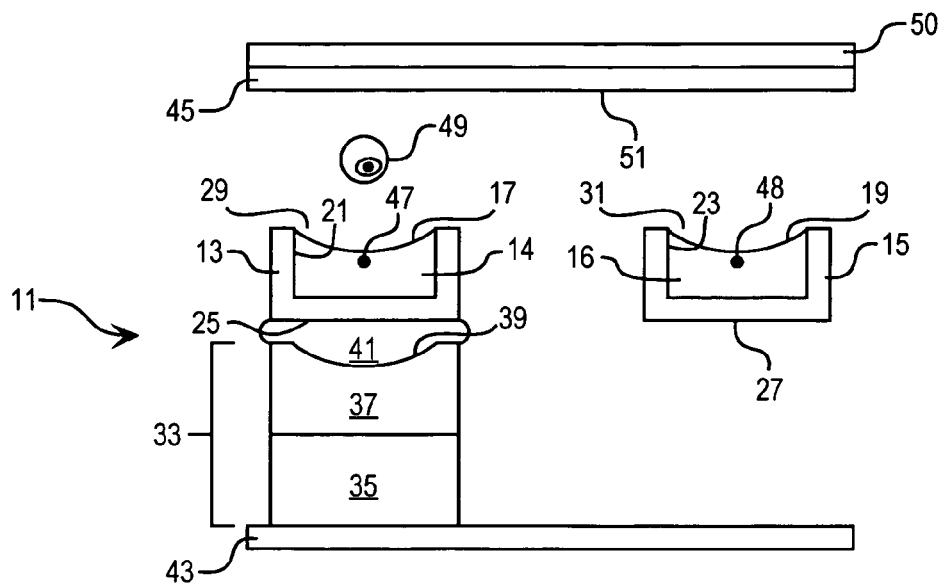
FIGS. 1A and 1B, collectively referred to as FIG. 1, schematically illustrate in simplified cross-sectional view an embodiment of a device useful in conjunction with the invention, the device comprising first and second cell containers or reservoirs, an acoustic ejector, and an ejector positioning means. As with all figures referenced herein, in which like parts are referenced by like numerals.

Before describing the present invention in detail, it is to be understood that this invention is not limited to specific fluids, cells, biomolecules, or device structures, as such may vary. It is also to be understood that the terminology used herein is for the purpose of describing particular embodiments only, and is not intended to be limiting.

It must be noted that, as used in this specification and the appended claims, the singular forms "a," "an," and "the" include plural referents unless the context clearly dictates otherwise. Thus, for example, reference to "a container" or "a reservoir" includes a single container or reservoir as well as a plurality of containers or reservoirs, reference to "a fluid" includes a single fluid or a combination and/or mixture of different fluids, reference to "a biomolecule" includes a single molecule as well as a combination and/or mixture of biomolecules, and the like.

In describing and claiming the present invention, the following terminology will be used in accordance with the definitions set out below.

The phrase "localized fluid volume" refers to a spatially localized volume of fluid. Typically, a localized fluid volume will have different physical properties than the surrounding fluid, although this is not required. In practice, a localized fluid volume can only be detected if its properties are different from those of the surrounding fluid. A sugar crystal suspended in an unsaturated (by the sugar) aqueous solution, and surrounded by a volume in which the sugar concentration of the local fluid is greater than the mean sugar concentration of the bulk fluid, is an example of an uncircumscribed localized fluid volume having no delineating or circumscribing structure. Other uncircumscribed localized fluid volumes include fluidic compositions wherein localized lipidic, or hydrophobic, regions are contained within a hydrophilic (e.g., aqueous) fluid, or wherein localized hydrophilic (e.g., aqueous) regions are contained within a lipidic, or hydrophobic fluid. Examples of such immiscible fluids are described in detail in U.S. patent applications Ser. Nos. 09/669,194 and 09/962,730 ("Method and Apparatus for Generating Droplets of Immiscible Fluids"), inventors Ellson and Mutz, filed on Sep. 25, 2000, and Sep. 25, 2001, respectively, and assigned to Picoliter Inc. (now Labcyte Inc. of Sunnyvale, Calif.).

A "circumscribed fluid volume" is a localized fluid volume that is delineated or circumscribed, usually by a structure, but possibly also by a potential well of an energy field. A biological cell is a prime example of a circumscribed fluid volume, as it is delineated by a cell membrane. Other examples of circumscribed fluid volumes include platelets, mitochondria, and nuclei, which are cell organelles or packaged cellular subdivisions. An example of a circumscribed volume not derived from a living organism is a fluid-containing microcapsule, wherein the capsule wall may or may not allow for some exchange of material between the capsule interior and the external fluid. The fluid in a circumscribed fluid volume may contain suspended solid and gel particles. By being circumscribed, however, the entire circumscribed volume behaves as a single particle unless the circumscribing structure or field is breached. A solid or gel particle, such as a glass or polymer bead, is included within the contemplated meaning of circumscribed volume; such a particle is circumscribed from the carrier fluid by virtue of the material from which it is made. Other types of circumscribed volumes are liposomes, micelles and reverse micelles, wherein an outer layer serves as a vesicle-encapsulating layer, and the vesicle interior is filled with a fluid. Still other types of circumscribed volumes are comprised of a first fluid that may or may not be immiscible with the fluid in which it is contained, wherein a molecular layer of an immiscible material circumscribes the first fluid so as to provide a barrier between the fluidic interior and the fluidic exterior.

Unless otherwise indicated, the term "cell" as used herein can also refer to a non-cellular localized fluid volume. Therefore, an ejected fluid droplet that is stated to contain a cell is to be interpreted as a fluid droplet that can contain a localized fluid volume that may or may not comprise a cell. Examples of other types of localized fluid volumes contained within a larger volume of fluid are provided above.

The term "fluid" as used herein refers to matter that is nonsolid or at least partially gaseous and/or liquid. A fluid may contain a solid that is minimally, partially, or fully solvated, dispersed, or suspended; particles comprised of gels or discrete fluids may also be suspended in a fluid. Examples of fluids include, without limitation, aqueous liquids (including water per se and salt water) and nonaqueous liquids such as organic solvents and the like. Live cells suspended in a carrier fluid represent an example of a gel or discrete fluid suspended in a fluid.

The term "near" is used to refer to the distance from the focal point of the focused acoustic radiation to the surface of the fluid from which a droplet is to be ejected. The distance should be such that the focused acoustic radiation directed into the fluid results in droplet ejection from the fluid surface, and one of ordinary skill in the art will be able to select an appropriate distance for any given fluid using straightforward and routine experimentation. Generally, however, a suitable distance between the focal point of the acoustic radiation and the fluid surface is in the range of about 1 to about 15 times the wavelength of the speed of sound in the fluid, more typically in the range of about 1 to about 10 times that wavelength, preferably in the range of about 1 to about 5 times that wavelength.

The term "reservoir" as used herein refers to a receptacle or chamber for holding or containing a fluid. Thus, a fluid in a reservoir necessarily has a free surface, i.e., a surface that allows a droplet to be ejected therefrom. As long as a fluid container has at least one free surface from which fluid can be ejected, the container is a reservoir regardless of specific geometry. Thus a "reservoir" includes, for example, a microfluidic channel containing flowing fluid from which droplets are ejected. A "cell container" or "cell reservoir" is a reservoir that is specialized for ejection of living cells suspended in a carrier fluid, and includes, by example, a microfluidic or other channel through which living cells flow suspended in a carrier fluid.

The terms "acoustic coupling" and "acoustically coupled" used herein refer to a state wherein an object is placed in direct or indirect contact with another object so as to allow acoustic radiation to be transferred between the objects without substantial loss of acoustic energy. When two entities are indirectly acoustically coupled, an "acoustic coupling medium" is needed to provide an intermediary through which acoustic radiation may be transmitted. Thus, an ejector may be acoustically coupled to a fluid, e.g., by immersing the ejector in the fluid or by interposing an acoustic coupling medium between the ejector and the fluid to transfer acoustic radiation generated by the ejector through the acoustic coupling medium and into the fluid.

The term "bound," as in, for example, a substrate surface having a cell "bound" thereto, includes covalent binding, adsorption, and physical immobilization. The term "attached" is identical in meaning to the term "bound" as used herein.

The term "adsorb" as used herein refers to the noncovalent retention of a molecule, molecular segment, or cell by a substrate surface. That is, adsorption occurs as a result of noncovalent interaction between a substrate surface and adsorbing moieties present on the entity that is adsorbed. Adsorption may occur through hydrogen bonding, van der Waal's forces, polar attraction or electrostatic forces (i.e., through ionic bonding). Often the substrate may be functionalized with adsorbent moieties to interact in a certain manner.

The term "array" used herein refers to a two-dimensional arrangement of features or materials, e.g., cells. Arrays are generally comprised of regular, ordered features, as in, for example, a rectilinear grid, parallel stripes, spirals, and the like, but non-ordered arrays may be advantageously used as well.

The terms "biomolecule" and "biological molecule" are used interchangeably herein to refer to any organic molecule, whether naturally occurring, recombinantly produced, or chemically synthesized in whole or in part, that is, was or can be a part of a living organism. The terms encompass, for example, nucleotides, amino acids and monosaccharides, as well as oligomeric and polymeric species such as oligonucleotides and polynucleotides, peptidic molecules such as oligopeptides, polypeptides and proteins, saccharides such as disaccharides, oligosaccharides, polysaccharides, mucopolysaccharides or peptidoglycans (peptido-polysaccharides) and the like. The term also encompasses ribosomes, enzyme cofactors, pharmacologically active agents, and the like.

The terms "focusing means" and "acoustic focusing means" refer to a means for causing acoustic waves to converge at a focal point by either a device separate from the acoustic energy source that acts like an optical lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as known in the art and described, for example, in U.S. Pat. No. 5,798,779 to Nakayasu et al. and Amemiya et al. (1997) *Proceedings of the 1997 IS&TNIP13 International Conference on Digital Printing Technologies Proceedings*, at pp. 698-702.

The term "substrate" as used herein refers to any material having a surface onto which one or more fluids may be deposited. The substrate may be constructed in any of a number of forms such as wafers, slides, well plates, membranes, for example. In addition, the substrate may be porous or nonporous as may be required for deposition of a particular fluid. Suitable substrate materials include, but are not limited to, supports that are typically used for solid phase chemical synthesis, e.g., polymeric materials (e.g., polystyrene, polyvinyl acetate, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, divinylbenzene styrene-based polymers), agarose (e.g., Sepharose®), dextran (e.g., Sephadex®), cellulosic polymers and other polysaccharides, silica and silica-based materials, glass (particularly controlled pore glass, or "CPG") and functionalized glasses, ceramics, and such substrates treated with surface coatings, e.g., with microporous polymers (particularly cellulosic polymers such as nitrocellulose), microporous metallic compounds (particularly microporous aluminum), antibody-binding proteins (available from Pierce Chemical Co., Rockford Ill.), bisphenol A polycarbonate, or the like. Porous substrates of particular interest include, without limitation: uncoated porous glass slides, including CPG slides; porous glass slides coated with a polymeric coating, e.g., an aminosilane or poly-L-lysine coating, thus having a porous polymeric surface; and nonporous glass slides coated with a porous coating. The porous coating may be a porous polymer coating, such as may be comprised of a cellulosic polymer (e.g., nitrocellulose) or polyacrylamide, or a porous metallic coating (for example, comprised of microporous aluminum). Examples of commercially available substrates having porous surfaces include the Fluorescent Array Surface Technology (FAST™) slides available from Schleicher & Schuell, Inc. (Keene, N.H.), which are coated with a 10-30 µm thick porous, fluid-permeable nitrocellulose layer that substantially increases the available binding area per unit area of surface. Other commercially available porous substrates include the CREATIVECHIP® permeable slides currently available from Eppendorf AG (Hamburg, Germany), and substrates having "three-dimensional" geometry, by virtue of an ordered, highly porous structure that enables reagents to flow into and penetrate through the pores and channels of the entire structure. Such substrates are available from Gene Logic, Inc. under the tradename "Flow-Thru Chip," and are described by Steel et al. in Chapter 5 of *Microarray Biochip Technology* (BioTechniques Books, Natick, Mass., 2000).

The term "porous" as in a "porous substrate" or a "substrate having a porous surface," refers to a substrate or surface, respectively, having a porosity (void percentage) in the range of about 1% to about 99%, preferably about 5% to about 99%, more preferably in the range of about 15% to about 95%, and an average pore size of about 100 Å to about 1 mm, typically about 500 Å to about 0.5 mm.

The term "impermeable" is used in the conventional sense to mean not permitting water or other fluid to pass through. The term "permeable" as used herein means not "impermeable." Thus, a "permeable substrate" and a "substrate having a permeable surface" refer to a substrate or surface, respectively, which can be permeated with water or other fluid.

While the foregoing support materials are representative of conventionally used substrates, it is to be understood that a substrate may in fact comprise any biological, nonbiological, organic and/or inorganic material, and may be in any of a variety of physical forms, e.g., particles, strands, precipitates, gels, sheets, tubing, spheres, containers, capillaries, pads, slices, films, plates, and the like, and may further have any desired shape, such as a disc, square, sphere, circle, etc. The substrate surface may or may not be flat, e.g., the surface may contain raised or depressed regions. A substrate may additionally contain or be derivatized to contain reactive functionalities. These are widely known and include, for example, silicon dioxide supports containing reactive Si—OH groups, polyacrylamide supports, polystyrene supports, polyethylene glycol supports, and the like.

The term "surface modification" as used herein refers to the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. Any of the substrate surfaces herein may be modified in one or more of the foregoing ways, and the term "surface" is intended to include modified surfaces as just described.

The term "binary" refers to a two-possibility selection scheme, for example ejection or non-ejection based upon the detection of a threshold level of fluorescence. The term "non-binary" refers to a selection scheme having more than two possible selections, for example ejection to a first target container based upon detection of a fluorescence emission greater than a high threshold, ejection to a second target container based upon fluorescence detected above the detection threshold, but below the high fluorescence threshold, and non-ejection if no fluorescence of a given frequency is detectable.

The term "colony of cells" or "cell colony" as used herein refers to one or more cells. In the case that a plurality of cells comprises the colony, the cells are sufficiently close that the environment or external conditions of a given single cell are affected by neighboring cells.

The term "substantially" as in, for example, the phrase "substantially all cells of an array," refers to at least 90%, preferably at least 95%, more preferably at least 99%, and most preferably at least 99.9%, of the cells of an array. Other uses of the term "substantially" involve an analogous definition.

"Optional" or "optionally" means that the subsequently described circumstance may or may not occur, so that the description includes instances where the circumstance occurs and instances where it does not.

In one embodiment, then, the invention pertains to a method for separating localized volumes within a fluid, wherein each localized volume has a different acoustic impedance than the fluid. A detector is used to identify the location of one localized volume and determine one or more properties thereof. Then, focused energy, preferably focused acoustic energy, is applied to the fluid in a manner effective to eject the localized volume from the fluid as a droplet. The device used is preferably an acoustic ejection device, comprising: one or more containers or reservoirs, each adapted to contain a carrier fluid within which living cells are suspended; an ejector comprising an acoustic radiation generator for generating acoustic radiation; a focusing means for focusing acoustic radiation at a focal point within and near the fluid surface in each of the reservoirs; and a means for positioning the ejector in acoustic coupling relationship to each of the reservoirs.

FIGS. 1 and 5 illustrate alternative embodiments of the employed device in simplified cross-sectional views. FIG. 1 depicts a cell ejection system where the container or reservoir is a conventional container, such as a conventional petri dish, which is radially symmetrical. In FIG. 5, the reservoir is a fluidic channel, through which, for example, live cells flow in a carrier fluid. The device 11 includes a plurality of cell containers or reservoirs, i.e., at least two containers or reservoirs, with a first container indicated at 13 and a second container indicated at 15, each adapted to contain a fluid, and each fluid having a fluid surface; e.g., a first cell container having cells suspended in fluid 14 and a second cell container having cells suspended in fluid 16, with fluid surfaces respectively indicated at 17 and 19. The carrier fluids of 14 and 16 and any cells suspended therein may be the same or different. As depicted, the containers or reservoirs are of substantially identical construction so as to be substantially acoustically indistinguishable, but identical construction is not a requirement. The containers are shown as separate removable components but may, if desired, be fixed within a plate or other substrate. For example, the plurality of containers in FIG. 1 may comprise individual wells in a well plate, optimally although not necessarily arranged in an array. Likewise, the plurality of containers in FIG. 5 may comprise separate channels or individual channels in a plate, for example a pattern of individual microfluidic channels etched into a plate as by photolithography. Each of the cell containers or reservoirs 13 and 15 is preferably bilaterally (FIG. 5) or axially (FIG. 1) symmetric. They each have substantially vertical walls 21 and 23 that extend upward from reservoir bases 25 and 27 and terminate at openings 29 and 31, respectively, although other reservoir shapes may be used, including those with fluidic channels having an aperture or opening for ejection at a specific location. The material and thickness of each container or reservoir base should be such that acoustic radiation may be transmitted therethrough and into the fluid contained within the reservoir.

The devices depicted in FIGS. 1 and 5 also include an acoustic ejector 33 comprised of an acoustic radiation generator 35 for generating acoustic radiation, and a focusing means 37 for focusing the acoustic radiation at a focal point within the fluid from which a droplet is to be ejected, near the fluid surface. As shown in FIGS. 1 and 5, the focusing means 37 may comprise a single solid piece having a concave surface 39 for focusing acoustic radiation, but the focusing means may be constructed in other ways as discussed below. The acoustic ejector 33 is thus adapted to generate and focus acoustic radiation so as to eject a droplet of fluid from each of the fluid surfaces 17 and 19 when acoustically coupled to reservoirs 13 and 15, and thus to fluids 14 and 16, respectively. The acoustic radiation generator 35 and the focusing means 37 may function as a single unit controlled by a single controller, or they may be independently controlled, depending on the desired performance of the device. Typically, single ejector designs are preferred over multiple ejector designs, because accuracy of droplet placement and consistency in droplet size and velocity are more easily achieved with a single ejector.

As will be appreciated by those skilled in the art, any of a variety of focusing means may be employed in conjunction with the present invention. For example, one or more curved surfaces may be used to direct acoustic radiation to a focal point near a fluid surface. One such technique is described in U.S. Pat. No. 4,308,547 to Lovelady et al. Focusing means with a curved surface have been incorporated into commercially available acoustic transducers such as those manufactured by Panametrics Inc. (Waltham, Mass.). In addition, Fresnel lenses are known in the art for directing acoustic energy at a predetermined focal distance from an object plane. See, e.g., U.S. Pat. No. 5,041,849 to Quate et al. Fresnel lenses may have a radial phase profile that diffracts a substantial portion of acoustic energy into a predetermined diffraction order at diffraction angles that vary radially with respect to the lens. The diffraction angles should be selected to focus the acoustic energy within the diffraction order on a desired object plane. Phased arrays of acoustic energy emitters have also been used to focus acoustic energy at a specified point as a result of constructive and destructive interference between the acoustic waves emitted by the arrayed sources (Amemiya et al. (1997) Proceedings of 1997 IS&T NIP13 International Conference on Digital Printing Technologies, pp. 698-702).

There are also a number of ways to acoustically couple the ejector 33 to each individual reservoir and thus to the fluid therein. One such approach is through direct contact, as is described, for example, in U.S. Pat. No. 4,308,547 to Lovelady et al., wherein a focusing means constructed from a hemispherical crystal having segmented electrodes is submerged in a liquid to be ejected. The aforementioned patent further discloses that the focusing means may be positioned at or below the surface of the liquid. This approach for acoustically coupling the focusing means to a fluid is, however, undesirable when the ejector is used to eject different fluids from a plurality of containers or reservoirs, as repeated cleaning of the focusing means would be required in order to avoid cross-contamination. The cleaning process would necessarily lengthen the transition time between each droplet ejection event. In addition, in such a method, cells in the fluid would adhere to the ejector as it is removed from a container, wasting cellular material that may be rare or irreplaceable. Finally, submersion in the fluid is not possible with conventional acoustic energy focusing means when the reservoirs are microfabricated, as when the cell containers are microfluidic channels or micro-wells, because the containers are too small.

One of skill in the art of microfabrication would be able to make a focusing means comprising a microfabricated, curved member. Similarly, a microfabricated focusing means constructed from a hemispherical crystal having segmented electrodes, e.g. a miniature focusing means as described in U.S. Pat. No. 4,308,547 to Lovelady et al., can be made by routine microfabrication techniques. Submersion would then be possible with the same disadvantages as above. For microfluidic channels or wells, then, a focusing means as well as a source of acoustic energy could be integrated into the microfabricated assembly.

An approach practicable for any reservoir dimensions would be to acoustically couple a conventional non-microfabricated or macro-scale ejector to the reservoirs and reservoir fluids without bringing any portion of the ejector, e.g., the focusing means, into contact with any of the fluids to be ejected. To this end, the present invention provides an ejector positioning means for positioning the ejector in controlled and repeatable acoustic coupling with each of the fluids in the cell containers or reservoirs to eject droplets therefrom without submerging the ejector therein. This method typically involves direct or indirect contact between the ejector and the external surface of each reservoir. When direct contact is used in order to acoustically couple the ejector to each reservoir, it is preferred that the direct contact is wholly conformal to ensure efficient acoustic energy transfer. That is, the ejector and the reservoir should have corresponding surfaces adapted for mating contact. Thus, if acoustic coupling is achieved between the ejector and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs having a specially formed inverse surface.

Figure 5A:
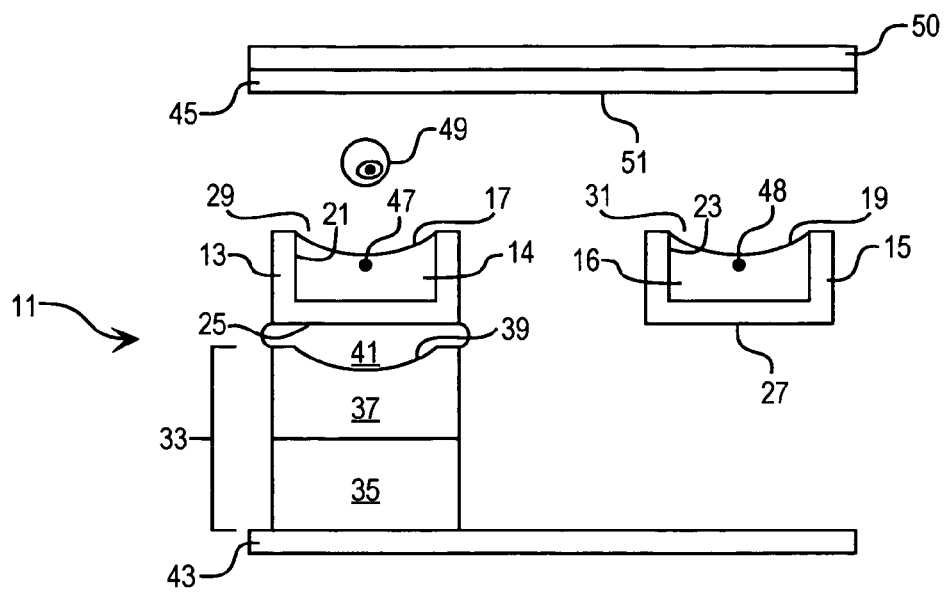
FIGS. 5A, 5B, 5C, 5D, and 5E, collectively referred to as FIG. 5, depict a device having a fluidic channel as the container from which the cells are ejected onto the substrate.

Optimally, acoustic coupling is achieved between the ejector and each of the reservoirs through indirect contact, as illustrated in FIGS. 1A and 5A. In the figures, an acoustic coupling medium 41 is placed between the ejector 33 and the base 25 of reservoir 13, with the ejector and reservoir located at a predetermined distance from each other. The acoustic coupling medium may be an acoustic coupling fluid, preferably an acoustically homogeneous material in conformal contact with both the acoustic focusing means 37 and each reservoir. In addition, it is important to ensure that the fluid medium is substantially free of material having different acoustic properties than the fluid medium itself. As shown, the first reservoir 13 is acoustically coupled to the acoustic focusing means 37 such that an acoustic wave is generated by the acoustic radiation generator and directed by the focusing means 37 into the acoustic coupling medium 41, which then transmits the acoustic radiation into the reservoir 13.

In operation, reservoirs 13 and 15 of the device are each filled with first and second carrier fluids having cells or cell mixtures 14 and 16 suspended therein, respectively, as shown in FIGS. 1 and 5. The acoustic ejector 33 is positionable by means of ejector positioning means 43, shown below reservoir 13, in order to achieve acoustic coupling between the ejector and the reservoir through acoustic coupling medium 41. Substrate 45 is positioned above and in proximity to the first reservoir 13 such that one surface of the substrate, shown in FIGS. 1 and 5 as underside surface 51, faces the reservoir and is substantially parallel to the surface 17 of the fluid 14 therein. Once the ejector, the reservoir, and the substrate are in proper alignment, the acoustic radiation generator 35 is activated to produce acoustic radiation that is directed by the focusing means 37 to a focal point 47 near the fluid surface 17 of the first reservoir. As a result, droplet 49 is ejected from the fluid surface 17 onto a designated site on the underside surface 51 of the substrate. The ejected droplet may be retained on the substrate surface by solidifying thereon after contact; in such an embodiment, it is necessary to maintain the substrate at a low temperature, i.e., a temperature that results in droplet solidification after contact. Alternatively, or in addition, a molecular moiety or marker moiety displayed on the surface of the droplet-contained cell attaches to the substrate surface after contact, through adsorption, mechanical immobilization, or covalent binding.

Figure 1B:
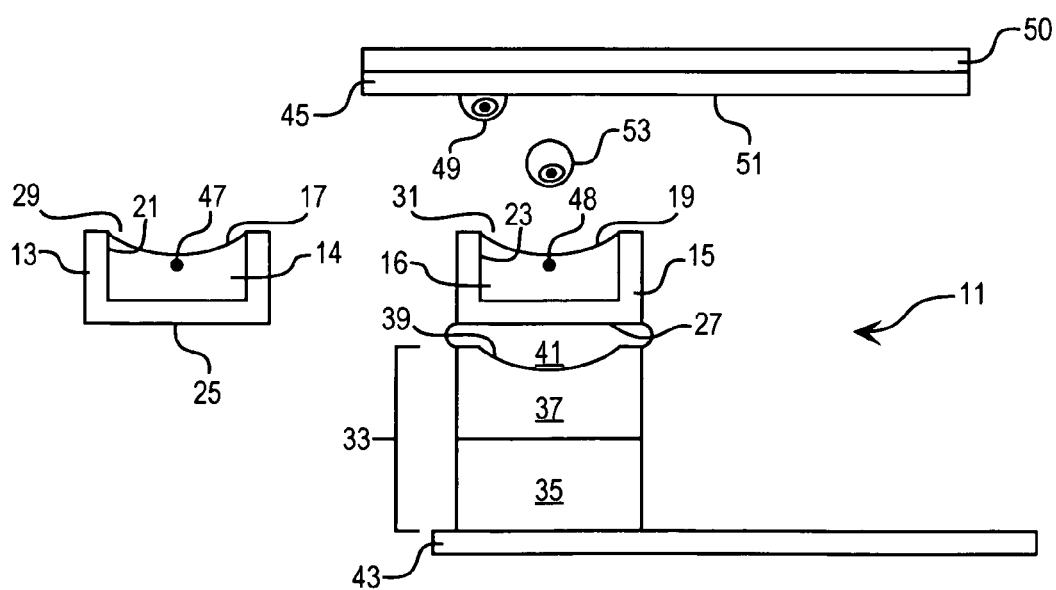
Figure 5B:
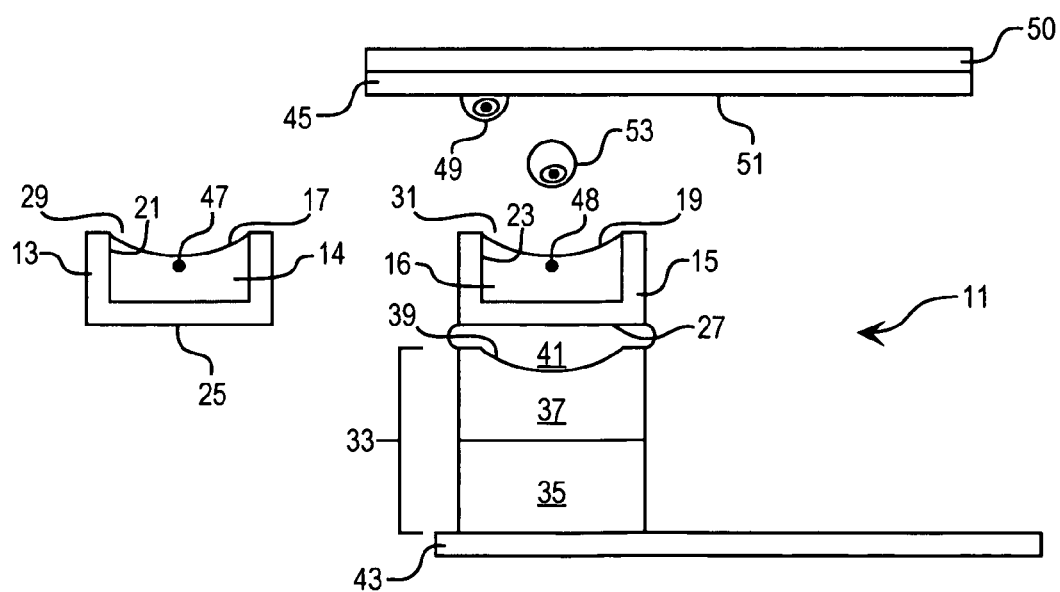
Figure 5C:
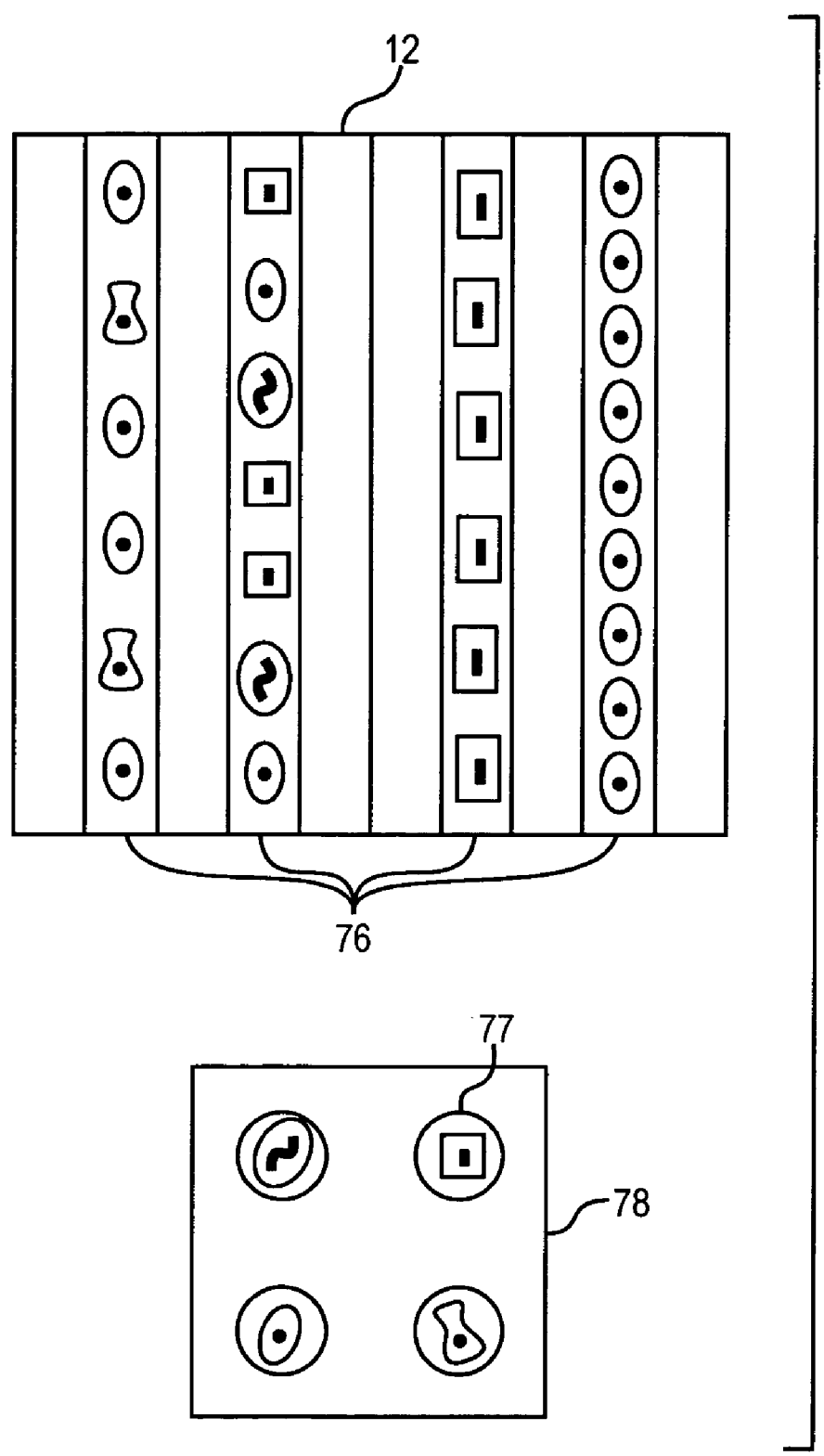

Next, as shown in FIGS. 1B and 5B, a substrate positioning means 50 repositions the substrate 45 over reservoir 15 in order to receive a droplet therefrom at a second designated site. FIGS. 1B and 5B also show that the ejector 33 has been repositioned by the ejector positioning means 43 below reservoir 15 and in acoustically coupled relationship thereto by virtue of acoustic coupling medium 41. Once properly aligned as shown in FIGS. 1B and 5B, the acoustic radiation generator 35 of ejector 33 is activated to produce acoustic radiation that is then directed by focusing means 37 to a focal point within fluid 16 near the fluid surface 19, thereby ejecting droplet 53 onto the substrate. It should be evident that such operation is illustrative of how the employed device may be used to eject a plurality of single cells contained in fluid droplets from reservoirs in order to form a pattern, e.g., an array, of cells on the substrate surface 51. It should be similarly evident that the device may be adapted to eject a plurality of individual cells contained in ejected fluid droplets from one or more reservoirs onto the same site of the substrate surface.

Figure 2A:
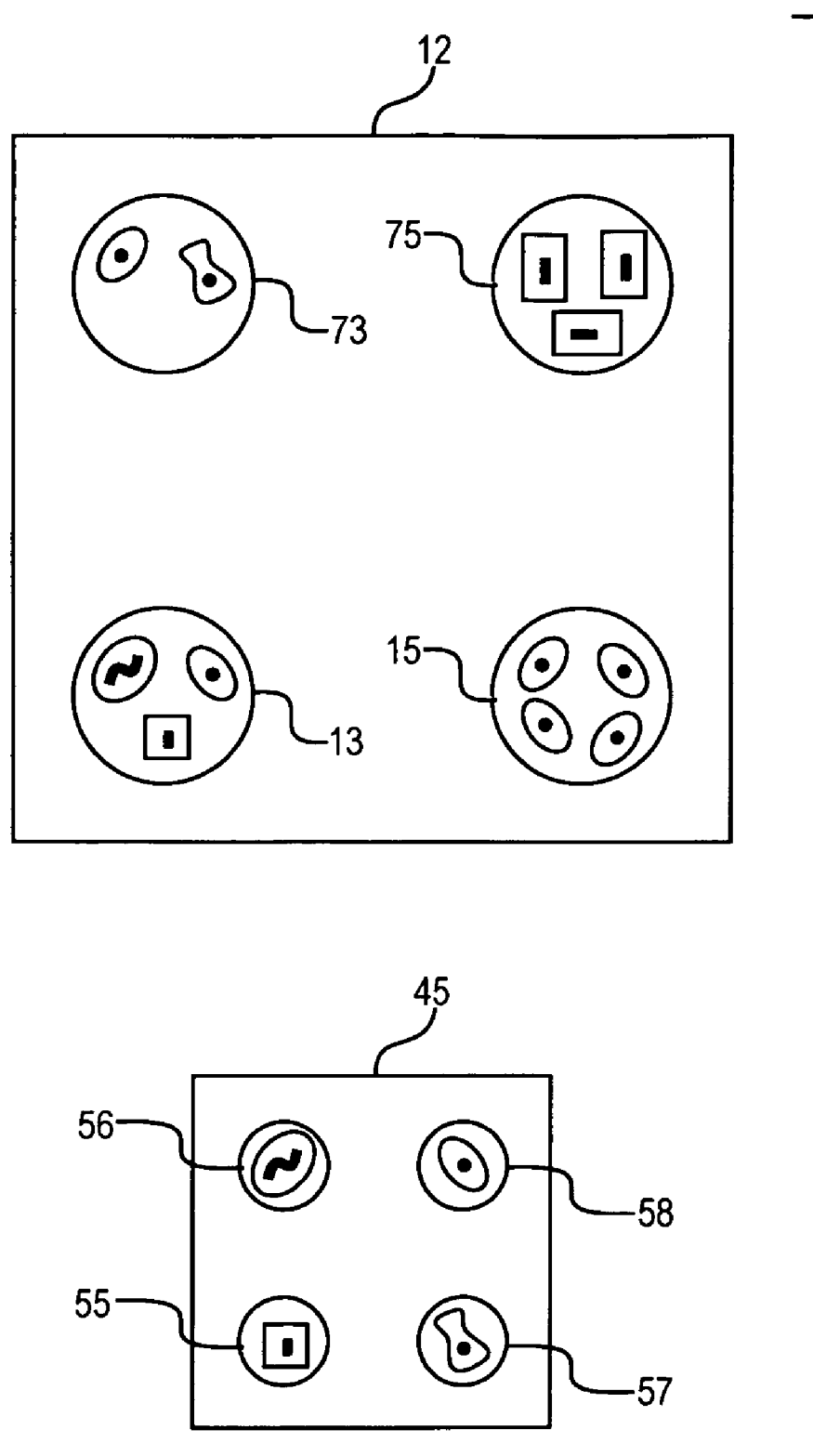
FIGS. 2A, 2B, and 2C, collectively referred to as FIG. 2, illustrate in schematic view a variation of the inventive embodiment of FIG. 1 wherein the cell containers or reservoirs comprise individual wells in a reservoir well plate, and the substrate comprises a smaller well plate with a corresponding number of wells.
Figure 2B:
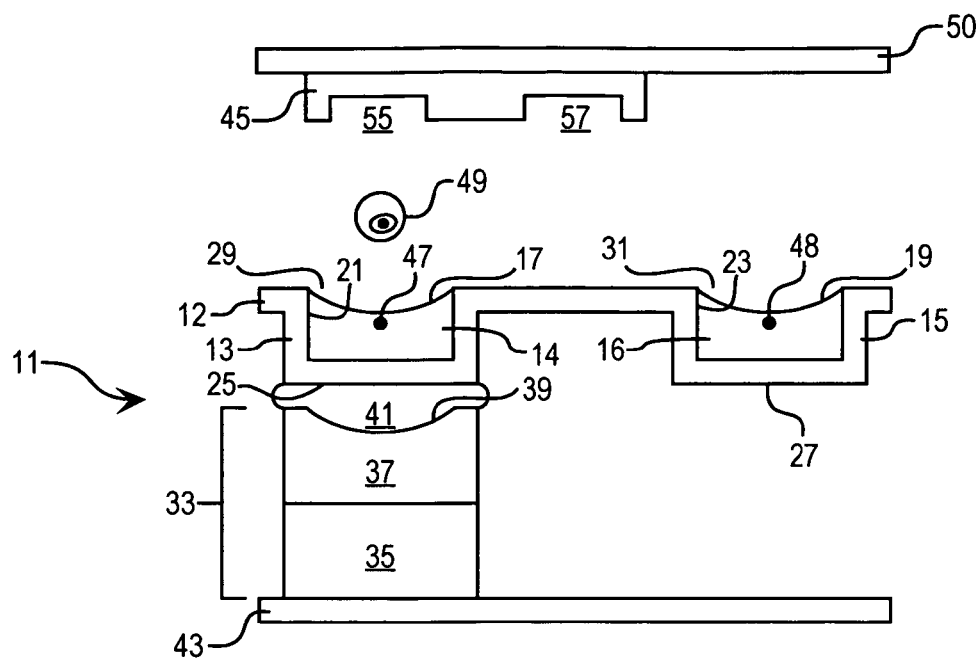

In another embodiment, the device is constructed so as to allow transfer of cells contained in fluid droplets between well plates, in which case the substrate comprises a substrate well plate, and the fluid-suspended-cell-containing reservoirs are individual wells in a reservoir well plate. FIG. 2 illustrates such a device, wherein four individual wells 13, 15, 73, and 75 in reservoir well plate 12 serve as fluid reservoirs for containing a plurality of a specific type of cell, or a mixture of different cell types, suspended in a fluid to be ejected as droplets containing a single cell, and the substrate comprises a smaller well plate 45 of four individual wells indicated at 55, 56, 57, and 58. FIG. 2A illustrates the cell container or reservoir well plate and the substrate well plate in top plane view. As shown, each of the well plates contains four wells arranged in a two-by-two array. FIG. 2B illustrates the employed device wherein the cell container or reservoir well plate and the substrate well plate are shown in cross-sectional view along wells 13, 15 and 55, 57, respectively As in FIGS. 1 and 5, reservoir wells 13 and 15 respectively contain cells suspended in carrier fluids 14 and 16 having carrier fluid surfaces respectively indicated at 17 and 19. The materials and design of the wells of the cell container or reservoir well plate are similar to those of the containers illustrated in FIGS. 1 and 5. For example, the cell containers or reservoirs shown in FIG. 2B (wells) and in FIG. 5B (channels) are of substantially identical construction so as to be substantially acoustically indistinguishable. In these embodiments, the bases of the cell reservoirs are of a material (e.g., a material having appropriate acoustic impedance) and thickness so as to allow efficient transmission of acoustic radiation therethrough into the contained carrier fluid.

The device of FIGS. 2 and 5 also includes an acoustic ejector 33 having a construction similar to that of the ejector illustrated in FIG. 1, comprising an acoustic generating means 35 and a focusing means 37. FIG. 2B shows the ejector acoustically coupled to a reservoir well through indirect contact; that is, an acoustic coupling medium 41 is placed between the ejector 33 and the reservoir well plate 12, i.e., between the curved surface 39 of the acoustic focusing means 37 and the base 25 of the first cell container or reservoir (well or channel) 13. As shown, the first cell container or reservoir (well or channel) 13 is acoustically coupled to the acoustic focusing means 37 such that acoustic radiation generated in a generally upward direction is directed by the focusing means 37 into the acoustic coupling medium 41, which then transmits the acoustic radiation into the cell container or reservoir (well or channel) 13.

In operation, each of the cell containers or reservoirs (well or channel) is preferably filled with a carrier fluid having a different type of cell or mixture of cells suspended within the carrier fluid. As shown, reservoir wells 13 and 15 of the device are each filled with a carrier fluid having a first cell mixture 14 and a carrier fluid having a second cell mixture 16, as in FIG. 1, to form fluid surfaces 17 and 19, respectively. FIGS. 1 and 5 show that the ejector 33 is positioned below reservoir well 13 by an ejector positioning means 43 in order to achieve acoustic coupling therewith through acoustic coupling medium 41.

For the ejection of individual cells into well plates from cell containers, FIG. 2A shows that the first substrate well 55 of substrate well plate 45 is positioned above the first reservoir well 13 in order to receive a droplet ejected from the first cell container or reservoir (well or channel).

Figure 5D:
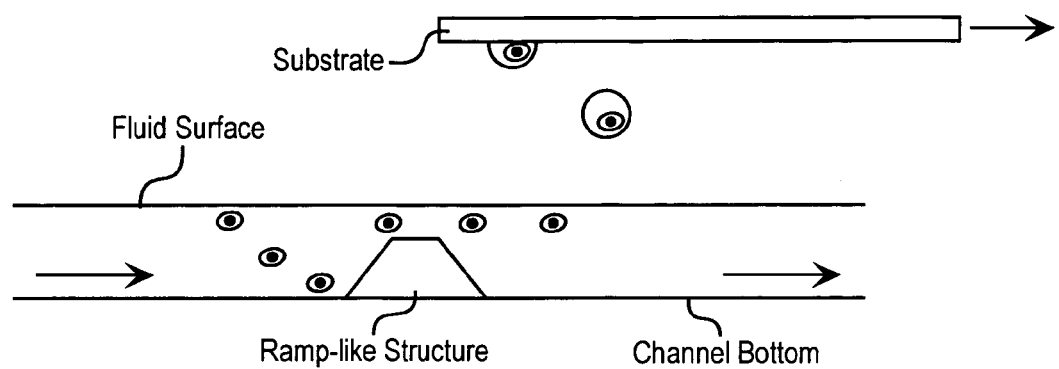
Figure 5E:
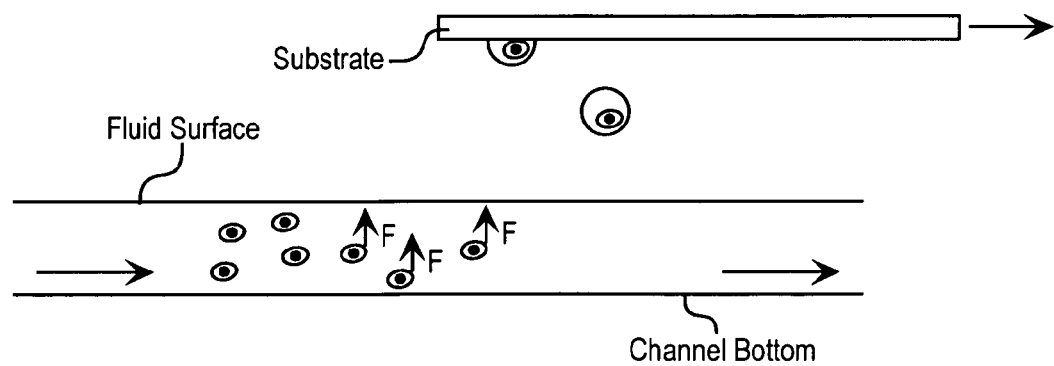

Once the ejector, the cell container or reservoir (well or channel), and the substrate are in proper alignment, the acoustic radiation generator is activated to produce an acoustic wave that is focused by the focusing means to direct the acoustic wave to a focal point 47 near fluid surface 17, with the amount of energy being insufficient to eject fluid. This first emission of focused acoustic energy permits sonic detection of the presence of a cell sufficiently close to the surface for ejection by virtue of reflection of acoustic energy, said reflection being due to a difference in acoustic impedance between the cell and the carrier fluid. Methods for determining the position of the cell by sonic detection are readily apprehended by those of ordinary skill in the art of acoustic microscopy and related arts. After a cell is detected and localized, other properties may be measured before the decision to eject is made: Also, if no cell is sufficiently close to the surface for ejection, the acoustic energy may be focused at progressively greater distances from the fluid surface until a cell is located and driven closer to the surface by focused acoustic energy or other means. For example, a uniform field may be used to move the cell closer to the surface. One such field is a photon field, which will exert a force based on cross-sectional area and change in photon momentum, determined by the difference in refractive indices of the carrier medium and the cells. Another such field that can be used to move cells is an electric field, which exerts a force based on net surface charge. A carrier fluid having a low density relative to the cells or a carrier fluid comprising a density gradient can also be used to position cells, as for ejection. It will be appreciated that there are numerous ways of effecting a short mean cell distance from the fluid surface. For channels, especially microfabricated channels, mechanical or fluidic means may be used to effect a sufficiently small distance from the fluid surface by placing a ramp-like structure across the channel, which decreases channel depth over the ramp to a depth on the order of the cell diameter, thereby only permitting cells to flow near the surface; cells are unlikely to jam at the ramp because the fluid velocity will be highest where the channel depth is lowest, as depicted in FIG. 5D. FIG. 5E depicts a microfluidic channel where a force acting on the cells moves them towards the surface.

Because microfluidic channels may be fabricated with small dimensions that reduce the volume in which a cell may be located, they are especially preferred for use with acoustic ejection, as locating a cell suitable for ejection is greatly simplified. For example, for a cell type or mixture of cell types having a relatively uniform size, for example a mean diameter of 10.0 µm, SD approx. 0.5 µm, the channel can be engineered to be about 12.0 µm wide, creating a single file of cells at a mean distance of about 1.0 µm from the fluid surface (ejection volume $4/3\pi r^3 = 0.52$ pL). In such a case it is not necessary to provide a ramp (FIG. 5D) or any other means to shorten the distance between the fluid surface and the cell location. The channel depth is as appropriate for desired fluid flow in the channel, but the channel is preferably equipped with a means for directing cells to a position sufficiently close to the surface for ejection (e.g., a channel depth no more than ten times the cell diameter). A specific example is to employ 40 µm deep channels that each has a ramp-like structure directing the cells to the surface, with a ramp height of about 25 µm. The cells can be ejected from the channel at a certain limited distance range along the fluid flow axis, reducing the area of fluid surface scanned. For example, a 50 µm aperture for ejecting cells can be provided in a closed capillary, or a limited distance along the flow axis of an open capillary may be used for ejection, a significant advantage being that the cells move past the ejector, reducing the area scanned for cells. Even when employing such methods to float cells in a macro-scale container such as a petri dish, significant amounts of time can be wasted scanning in the plane parallel to the fluid surface to locate a cell to eject. The advantages of employing microfluidic channels are only slightly diminished for a wider range of cell sizes; for example, red blood cells (RBC, mean diameter of 7 µm, SD0.3 µm, biconcave disc, height 3 µm) mixed with the preceding cell type (mean diameter of 10.0 µm, SD0.5 µm). Although the RBCs can be a significant depth from the surface relative to the fluid ejection volume, and thus significant energy would be required to eject a RBC, this situation can be overcome by the described methods of forcing cells toward the fluid surface. The advantage of limiting the lateral search to a width of about 12 µm, as opposed to the several cm width of a petri dish, is immediately apparent.

Once a cell sufficiently close to the surface is located and is determined to meet any other criteria for ejection, the acoustic radiation generator is activated to produce an acoustic wave that is focused by the focusing means to a focal point 47 near fluid surface 17, with the amount of energy being sufficient to eject a volume of fluid substantially corresponding to the volume of the cell to be ejected, so that any ejected volume does not contain more than one cell. The precise amount of energy required to eject only the required volume and no more can be initially calibrated by slowly increasing the energy applied, from an amount insufficient to eject a cell desired for ejection, until there is just enough energy applied to eject the cell the desired distance to the targeted substrate locale. After this initial calibration, approximately the same energy, with adjustment for any change in fluid level, may be applied to eject cells of substantially the same volume as the initial calibration cell. As a result, droplet 49, containing a single living cell, is ejected from fluid surface 17 into the first substrate well 55 of the substrate well plate 45. The cell-containing droplet is retained on the substrate well plate by surface tension.

Figure 2C:
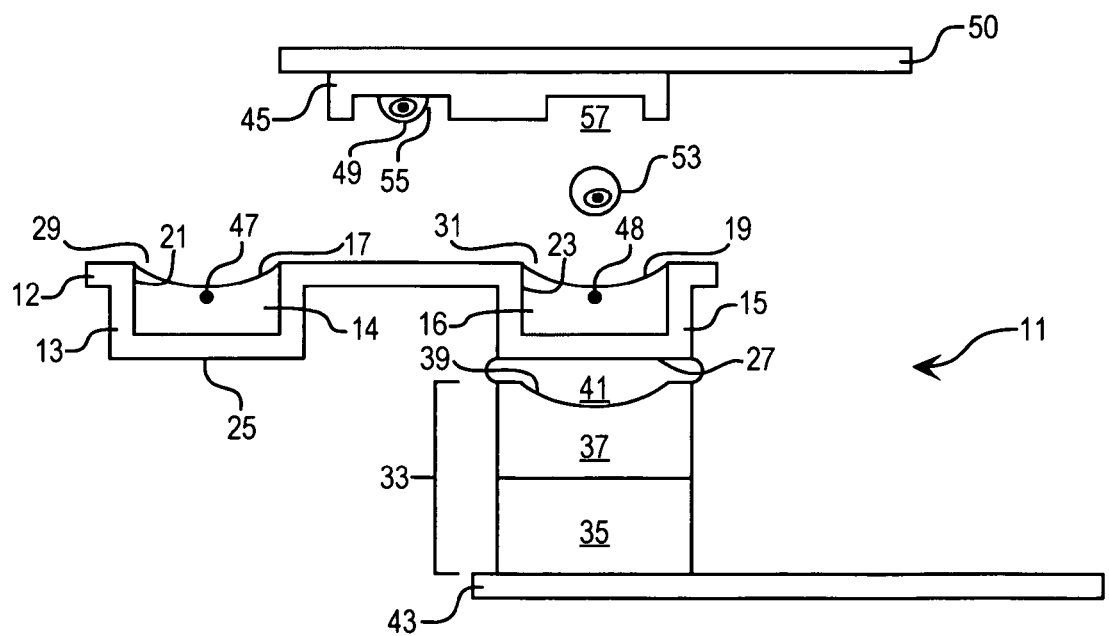

Then, as shown in FIG. 2C, the substrate well plate 45 is repositioned by a substrate positioning means 50 such that the substrate well 57 is located directly over the cell container or reservoir (well or channel) 15 in order to receive a cell-containing droplet therefrom. FIG. 2C also shows that the ejector 33 has been repositioned by the ejector positioning means below cell container well 15 to acoustically couple the ejector and the container through acoustic coupling medium 41. Since the substrate well plate and the reservoir well plate or channels on a planar substrate are of different sizes, there is only correspondence, not identity, between the movement of the ejector positioning means and the movement of the substrate well plate. Once properly aligned, as shown in FIG. 2C, the acoustic radiation generator 35 of ejector 33 is activated to produce an acoustic wave that is then directed by focusing means 37 to a focal point near the fluid surface 19; this wave is used to detect the presence of a cell that is sufficiently close to the carrier fluid surface to be ejected. After such a cell is detected, and any properties that are used as criteria for ejection are measured, the acoustic radiation generator 35 of ejector 33 is activated to produce an acoustic wave that is then directed by focusing means 37 to a focal point near the fluid surface 19 from which cell-containing droplet 53 is ejected onto the second well of the substrate well plate. It should be evident that such operation is illustrative of how the employed device may be used to transfer a plurality of single cells contained in appropriately sized droplets from one well plate to another of a different size. One of ordinary skill in the art will recognize that this type of transfer may be carried out even when the cells, the carrier fluid, the ejector, and the substrate are in continuous motion. It should be further evident that a variety of combinations of reservoirs, well plates, and/or substrates may be used in the employed device to transfer fluid droplets containing single cells. It should be still further evident that any reservoir may be filled with a fluid carrier, or with a fluid carrier containing suspended cells, through acoustic ejection of cell-free or cell-containing fluid droplets, respectively, prior to deploying the reservoir for further transfer of fluid droplets containing cells, e.g., for cell array deposition.

As discussed above, either individual (e.g., removable) reservoirs (well or channel) or plates (well or channel) may be used to contain cell suspensions in carrier fluids for ejection; the reservoirs or the wells of the well plate are preferably substantially acoustically indistinguishable from one another. Also, unless it is intended that the ejector be submerged in the fluid, the reservoirs or well plates must have acoustic transmission properties sufficient to allow acoustic radiation from the ejector to be conveyed to the surfaces of the fluids to be ejected. Typically, this involves providing reservoirs or well bases that have appropriate acoustic impedance relative to the carrier fluid, and are sufficiently thin relative to the acoustic attenuation of the material from which they are made, to allow acoustic radiation to travel therethrough without unacceptable dissipation or reflection. In addition, the material used in the construction of reservoirs must be compatible with the contained carrier fluids, and be non-toxic to the suspended cells.

Thus, as the reservoirs or wells are intended to contain live cells suspended in an aqueous carrier fluid, reservoirs made from materials that dissolve or swell in water or release compounds toxic to living cells into the aqueous carrier would be unsuitable for use in forming the reservoirs, substrates, or well plates employed in the instant invention. For water-based fluids, a number of materials are suitable for the construction of reservoirs; these include, but are not limited to, materials used for tissue or cell culture, biomaterials, mono- or polycrystalline silicon, ceramics such as silicon oxide and aluminum oxide, metals such as stainless steel and platinum, and polymers such as polyester and polytetrafluoroethylene. These materials may be prepared so that substances toxic to cells do not leach into the carrier fluid in sufficient amounts to render the carrier fluid toxic to the cells, and so that their surface properties are appropriate for the intended use. For example, containers or reservoirs from which cells are ejected may be surface-functionalized to prevent cell adhesion to the solid wall or floor of the container material.

Many well plates suitable for use with the employed device are commercially available and may contain, for example, 96, 384, or 1536 wells per well plate. Manufactures of suitable well plates for use in the employed device include Coming Inc. (Coming, N.Y.) and Greiner America, Inc. (Lake Mary, Fla.). The availability of such commercially available well plates does not, however, preclude the manufacture and use of custom-made well plates containing at least about 10,000 wells, or as many as 100,000 wells, or more. For array-forming applications, it is expected that about 100,000 to about 4,000,000 reservoirs may be employed. In addition, to reduce the amount of movement needed to align the ejector with each reservoir or reservoir well, it is preferable that the center of each reservoir be located not more than about 1 centimeter, preferably not more than about 1 millimeter, and optimally not more than about 0.5 millimeter, from any other reservoir center.

Generally, the device may be adapted to eject fluids of virtually any type and amount desired. The ejected fluid may be aqueous and/or nonaqueous, though only aqueous fluids are compatible with the transfer of living cells. Examples of aqueous fluids include water per se, water-solvated ionic and non-ionic solutions, gels, suspensions or slurries of solids, and aqueous liquids containing discrete cells. Because of the precision that is possible using the inventive technology, the device may be used to eject droplets from a reservoir adapted to contain no more than about 100 nanoliters of fluid, preferably no more than about 10 nanoliters of fluid. In certain cases, the ejector may be adapted to eject a droplet from a reservoir adapted to contain about 1 to about 100 nanoliters of fluid. This is particularly useful when the fluid to be ejected contains rare or expensive biomolecules or cells, wherein it may be desirable to eject droplets having a volume of about up to 1 picoliter.

From the above descriptions, it is evident that various components of the device may require individual control or synchronization to form an array of cells on a substrate. For example, the ejector positioning means may be adapted to eject droplets from each cell container or reservoir in a predetermined sequence associated with an array to be prepared on a substrate surface. Similarly, the substrate positioning means for positioning the substrate surface with respect to the ejector may be adapted to position the substrate surface to receive droplets in a pattern or array thereon. Either or both positioning means, i.e., the ejector positioning means and the substrate positioning means, may be constructed from, e.g., levers, pulleys, gears, linear motors, a combination thereof, or other mechanical means known to one of ordinary skill in the art. It is preferable to ensure that there is a correspondence between the movement of the substrate, the movement of the ejector, and the activation of the ejector to ensure proper pattern formation.

Moreover, the device may include other components that enhance performance. For example, as alluded to above, the device may further comprise a means for regulating temperature to ensure sample stability. One example of temperature regulation is lowering the temperature of the substrate surface to ensure, for example, that the ejected droplets adhere to the substrate and that cells rapidly freeze to maintain their viability. The cooling means may be adapted to maintain the substrate surface at a temperature that allows fluid to partially, or preferably completely, freeze shortly after the cell-containing fluid droplet comes into contact with it. In the case of aqueous fluid droplets that contain cells, the temperature regulation means may have the capacity to maintain the substrate surface at a temperature within a wide range, such as between −80° C. and 80° C., depending on the cell type and goal of assay being performed.

In addition, repeated application of acoustic energy to a reservoir of fluid may result in heating of the fluid. Heating can, of course, result in unwanted effects on living cells. Thus, the device may further comprise means for maintaining fluid in the cell containers or reservoirs at a constant temperature. Design and construction of such temperature-maintaining means are known to one of ordinary skill in the art and may comprise, e.g., components such a heating element, a cooling element, a temperature-sensing means such as a thermocouple, or a combination thereof. For biomolecular and live cell deposition applications, it is generally desired that the fluid containing the biomolecule or cells be kept at a constant temperature, with deviations of no more than about 1° C. or 2° C. In addition, for live cells, it is preferred that the fluid be kept at a temperature that does not exceed about 1° C. above the normal temperature from which the cell is derived in the case of warm blooded organisms, and between 16° C. and 37° C. for all other organisms, whether prokaryotic or eukaryotic, except for specific cell types known to have poor viability unless chilled. Cells that require chilling for viability will be appreciated by those of ordinary skill in the art of culturing and maintaining cells to require a saline carrier fluid of appropriate osmolality (slightly hyperosmotic) at about at about −1° C.± about 1° C. Thus, for example, when the biomolecule-containing fluid is aqueous, it may be optimal to keep the fluid at about −1° C.± about 0.5° C. during ejection.

The invention may involve modification of a substrate surface prior to receiving acoustically ejected cell-containing fluid droplets. Surface modification may involve functionalization or defunctionalization, smoothing or roughening, coating, degradation, passivation, or other alterations of the surface's chemical composition or physical properties. In one embodiment, the invention requires functionalization with a moiety cognate to an externally displayed marker moiety, but other surface modifications described may affect the success of the inventive method in a specific context One such surface modification method involves altering the wetting properties of the surface. Such a method can be used, for example, to facilitate confinement of a cell contained in a droplet ejected onto the surface within a designated area, or to enhance the surface attachment of molecular moieties used for functionalizing the substrate or a specific substrate locale (such as patterned biotinylation accomplished by acoustic ejection of a biotinylating solution). A preferred method for altering the wetting properties of the substrate surface involves deposition of droplets of a suitable surface modification fluid at each designated site of the substrate surface prior to acoustic ejection of fluids to form an array thereon. In this way, the "spread" of the acoustically ejected droplets and contained cells may be optimized, and consistency in spot size (i.e., diameter, height, and overall shape) ensured. One way to implement the method involves acoustically coupling the ejector to a modifier reservoir containing a surface modification fluid and then activating the ejector, as described in detail above, to produce and eject a droplet of surface modification fluid toward a designated site on the substrate surface. The method is repeated as desired to deposit surface modification fluid at additional designated sites. Similarly, by the methods of copending applications U.S. Ser. No. 09/964,193 ("Focused Acoustic Energy in the Preparation and Screening of Combinatorial Libraries," inventors Mutz and Ellson), filed Sep. 25, 2001, and U.S. Ser. No. 09/963,173 ("Focused Acoustic Energy in the Preparation of Peptide Arrays," inventors Mutz and Ellson), also filed Sep. 25, 2001, both of which are assigned to Picoliter Inc. (now Labcyte Inc. of Sunnyvale, Calif.) or by other methods of generating arrays of biomolecules attached or linked to a substrate surface, cognate moieties that specifically bind to marker moieties displayed on the surface of transformed or untransformed cells may be patterned on the substrate surface. Alternatively, a single cognate moiety such as biotin can be linked to the substrate surface either uniformly, or in a pattern (such as a pattern of biotinylated areas surrounded by non-biotinylated areas). The cells to be patterned can be transformed to display streptavidin on their surface.

FIG. 3 schematically illustrates in simplified cross-sectional view a specific embodiment of the aforementioned method, in which two cells are deposited at different sites on a substrate using a device similar to that illustrated in FIG. 1, but including an additional reservoir 59, which may contain a different type of cell, or may contain a surface modification fluid, the fluid 60 having a fluid surface 61. FIG. 3A illustrates the ejection of a droplet 63 (here depicted containing a cell rather than a surface modification fluid) of surface modification fluid or carrier-fluid-containing cells 60. When desired, a surface modifier may be employed for various purposes; for example, a surface modifier may be selected to alter the wetting properties of designated sites on the surface 51 of the substrate 45 where the cells are to be deposited. The ejector 33 is positioned by the ejector positioning means 43 below the modifier reservoir 59 in order to achieve acoustic coupling therewith through an acoustic coupling medium 41. Substrate 45 is positioned above the modifier reservoir 19 at a location that enables acoustic deposition of a droplet of surface modification fluid 60 at a designated site. Once the ejector 33, the modifier reservoir 59, and the substrate 45 are in proper alignment, the acoustic radiation generator 35 is activated to produce acoustic radiation that is directed by the focusing means 37 in a manner that enables ejection of a droplet 63 of the surface modification fluid 60 from the fluid surface 61 onto a designated site on the underside surface 51 of the substrate. Once the droplet 63 contacts the substrate surface 51, the droplet modifies an area of the substrate surface to result in an increase or decrease in the surface energy of the area with respect to the deposited fluids.

Figure 3A:
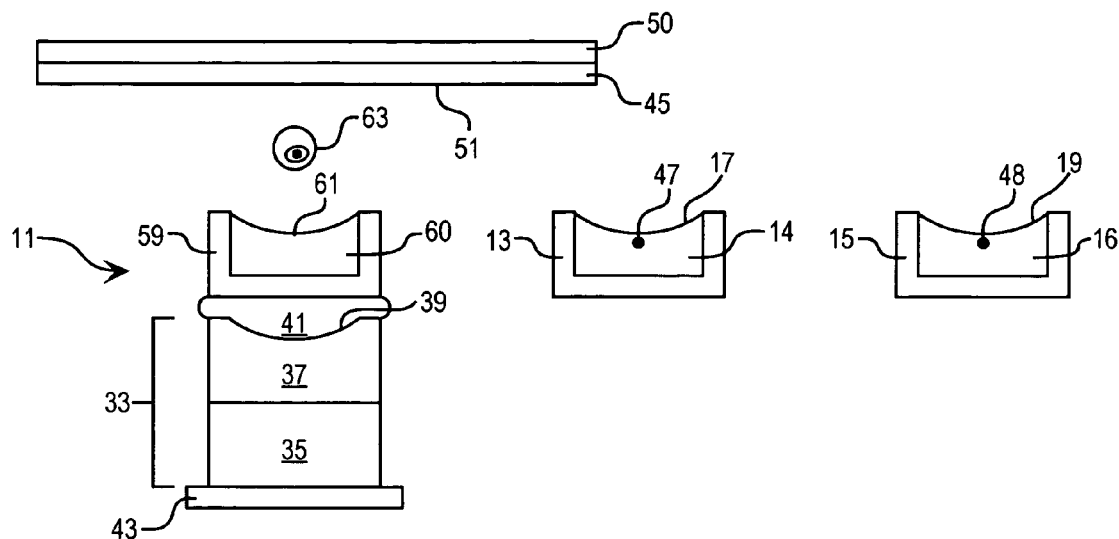
FIGS. 3A, 3B, 3C, and 3D, collectively referred to as FIG. 3, schematically illustrate in simplified cross-sectional view an embodiment of the inventive method in which cells having an externally displayed marker moiety are ejected onto a substrate using the device of FIG. 1.
Figure 3B:
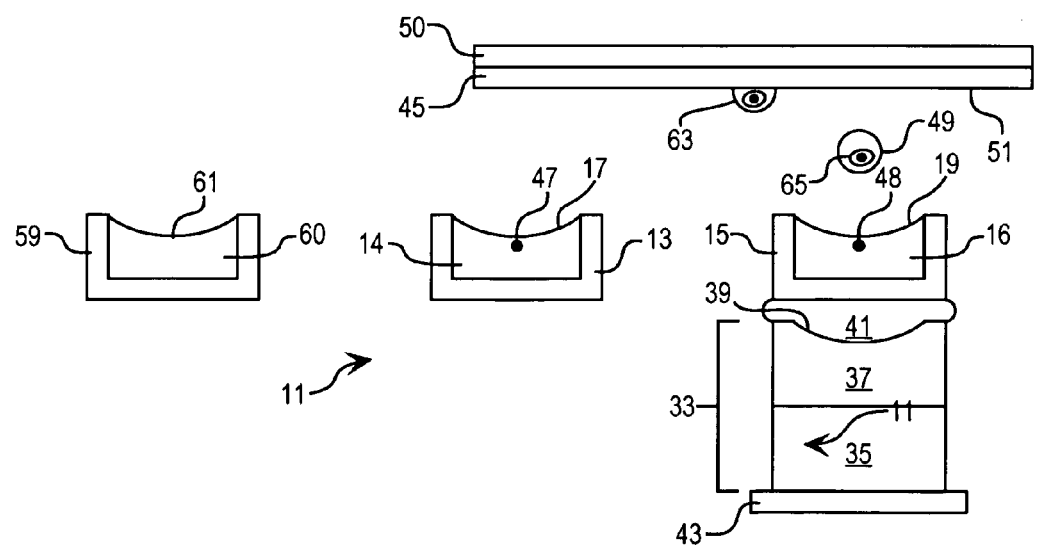

Next, as shown in FIG. 3B, the substrate 45 is repositioned by the substrate positioning means 50 such that the region of the substrate surface modified by the droplet 63 is located directly over the reservoir 13. FIG. 3B also shows that the ejector 33 is positioned by the ejector positioning means below reservoir 13 to acoustically couple the ejector and the reservoir through the acoustic coupling medium 41. Once properly aligned, the ejector 33 is again activated so as to eject droplet 49 onto the substrate. Droplet 49 contains a single cell 65, preferably displaying a marker moiety on its external cell membrane that is specifically bound by a cognate moiety linked to the surface, to effect specific attachment to the surface. The marker moiety may occur in an untransformed cell or may be the result of transformation or genetic manipulation, and may optionally signify transformation such that a gene other than the marker is expressed, e.g. the marker is a reporter of transformation by another gene.

Figure 3C:
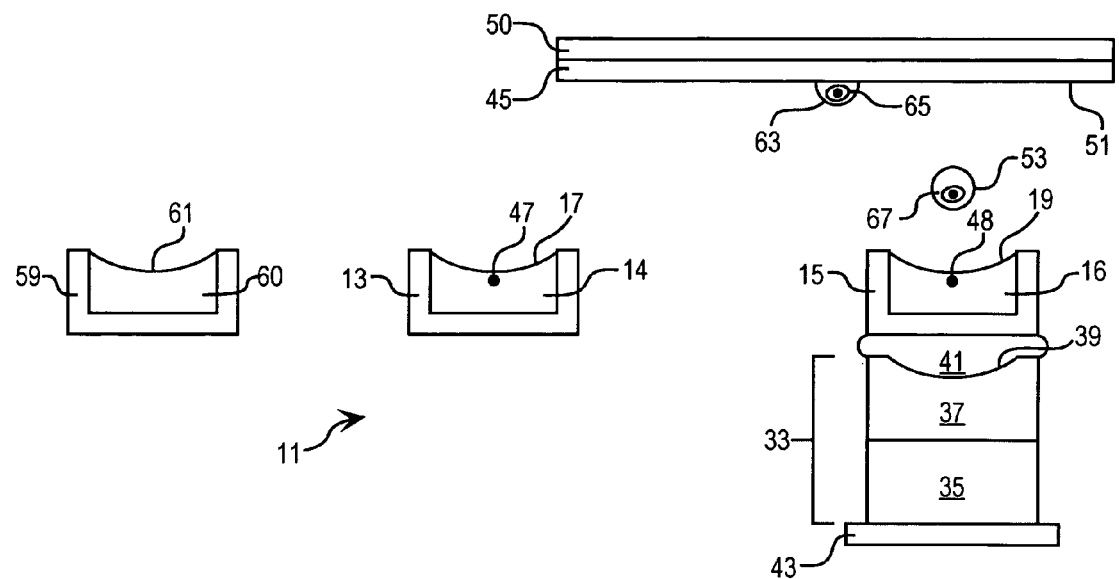
Figure 3D:
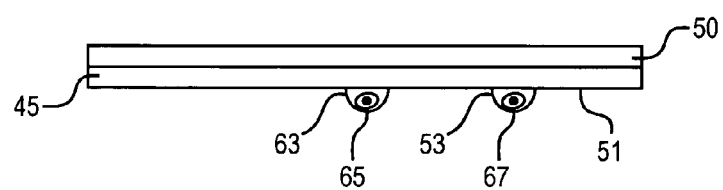
Figure 4A:
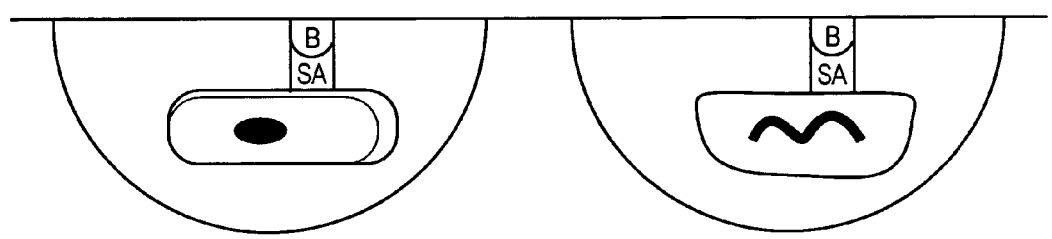
FIGS. 4A and 4B, collectively referred to as FIG. 4, depict arrayed cells contained in droplets deposited by acoustic ejection using the device of FIG. 1.
Figure 4B:
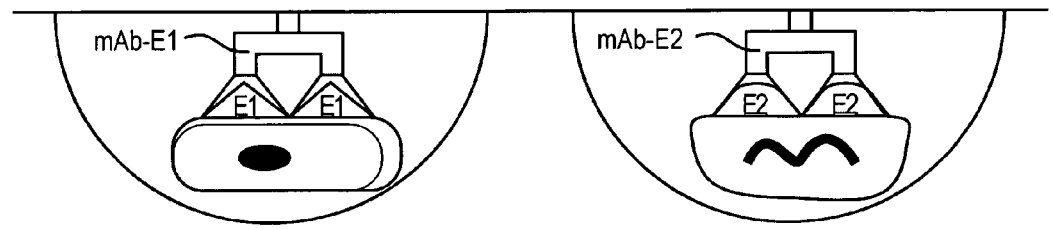

As shown in FIG. 3C, the substrate 45 is again repositioned by the substrate positioning means 50 such that a different site than the site where the first single cell 65 is attached is located directly over the reservoir 15 in order to receive a cell contained in a droplet therefrom. FIG. 3B also shows that the ejector 33 is positioned by the ejector positioning means below reservoir 15 to acoustically couple the ejector and the reservoir through an acoustic coupling medium 41. Once properly aligned, the ejector 33 is again activated so that droplet 53 is ejected onto the substrate. Droplet 53 contains a second single cell.

Cognate moieties are commonly ligands, including oligonucleotides and peptides. Marker moieties are likely to be peptides or peptidoglycans. The chemistry employed in synthesizing substrate-bound oligonucleotides can be adapted to acoustic fluid droplet ejection (see co-pending patent application U.S. Ser. No. 09/669,996, entitled "Acoustic Ejection of Fluids from a Plurality of Reservoirs," inventors Ellson, Foote, and Mutz, filed on Sep. 25, 2000 and assigned to Picoliter Inc. (now Labcyte Inc. of Sunnyvale, Calif.)). These methods may be used to create arrays of oligonucleotides on a substrate surface for use with the instant invention. Such adaptation will generally involve now-conventional techniques known to those skilled in the art of nucleic acid chemistry and/or described in the pertinent literature and texts. See, for example, DNA MICROARRAYS: A PRACTICAL APPROACH, M. Schena, Ed. (Oxford University Press, 1999). That is, the individual coupling reactions are conducted under standard conditions used for the synthesis of oligonucleotides and are conventionally accomplished with automated oligonucleotide synthesizers. Such methodology is described, for example, in D. M. Matteuci et al. TET. LETT. 521:719 (1980); U.S. Pat. No. 4,500,707 to Caruthers et al.; and U.S. Pat. Nos. 5,436,327 and 5,700,637 to Southern et al. Focused acoustic energy may also be adapted for in situ combinatorial oligonucleotide, oligopeptide, and oligosaccharide syntheses; these syntheses may be used to produce combinatorial arrays for use with the instant invention (see co-pending patent application U.S. Ser. No. 09/964,193, entitled "Focused Acoustic Energy in the Preparation and Screening of Combinatorial Composition of Libraries," inventors Mutz and Ellson).

Alternatively, an oligomer may be synthesized prior to attachment to the substrate surface and then spotted onto a particular locus on the surface using the methodology of the invention. Again, the oligomer may be an oligonucleotide, an oligopeptide, an oligosaccharide, or any other biomolecular (or nonbiomolecular) oligomer moiety. Preparation of substrate-bound peptidic molecules, e.g., those used in the formation of peptide arrays and protein arrays, is described in co-pending patent application U.S. Ser. No. 09/669,997 ("Focused Acoustic Energy in the Preparation of Peptidic Arrays"), inventors Mutz and Ellson, filed on Sep. 25, 2000 and assigned to Picoliter Inc. (now Labcyte Inc. of Sunnyvale, Calif.). Preparation of substrate-bound oligonucleotides, particularly arrays of oligonucleotides wherein at least one of the oligonucleotides contains partially nonhybridizing segments, is described in co-pending patent application U.S. Ser. No. 09/669,267 ("Arrays of Oligonucleotides Containing Nonhybridizing Segments"), inventor Ellson, also filed on Sep. 25, 2000 and assigned to Picoliter Inc. (now Labcyte Inc. of Sunnyvale, Calif.).

These acoustic ejection methods for use with the instant invention enable preparation of molecular arrays, particularly biomolecular arrays, having densities substantially higher than those possible using current array preparation techniques, such as photolithographic processes, piezoelectric techniques (e.g., using inkjet printing technology), and microspotting. The array densities that may be achieved using the devices and methods of the invention are at least about 1,000,000 biomolecules per square centimeter of substrate surface, preferably at least about 1,500,000 per square centimeter of substrate surface. The biomolecular moieties may be, e.g., peptidic molecules and/or oligonucleotides. Such densities commonly are not necessary for creating sites containing individual cells, which are separated by a distance from other cells. But adaptation of such methods, for example, to functionalize a discrete portion of a site surface with a cognate moiety that specifically binds a marker moiety, may be useful for localizing the cells within the site, or for deliberately arraying the cells in close proximity to each other. For example, a lymphocyte array (consisting of small (8 µm), medium (12 µm), odarge (14 µm) diameter cells), may be created by functionalizing a 10 µm diameter spot in the center of each 100 µm×100 µm site witl the appropriate cognate moiety to specifically bind the spotted cell. This arrangement would ensure sufficient cell separation to allow, for example, testing or screening of individual cells. The testing may be performed, for example, by acoustic deposition of reagent-containing fluid droplets of sufficient volume to expose or treat a cell, without exposing cells at adjacent sites to the fluid. Such a method would permit, for example, combinatorial screening of cells.

It should be evident, then, that many variations of the invention are possible. For example, each of the ejected droplets may be deposited as an isolated and "final" feature. Alternatively, or in addition, a plurality of ejected droplets, each containing one or a plurality of cells, may be deposited at the same location on a substrate surface in order to synthesize a cell array where each site contains multiple cells of ascertainable number. This method may be used to pattern cells for other purposes, such as to engineer a tissue based on the replication of a specific histologic architecture. For cell array and patterning fabrication techniques that involve attachment of cells to a substrate surface, it is expected that washing steps may be used between droplet ejection steps. Such washing steps may involve, e.g., submerging the entire substrate surface on which cells have been deposited in a washing fluid.

The invention enables the ejection of droplets at a rate of at least about 1,000,000 droplets per minute from the same reservoir, and at a rate of at least about 100,000 drops per minute from different reservoirs. In addition, current positioning technology allows for the ejector positioning means to move from one cell container or reservoir to another quickly and in a controlled manner, thereby allowing fast and controlled ejection of different fluids. That is, current commercially available technology allows the ejector to be moved from one reservoir to another, with repeatable and controlled acoustic coupling at each reservoir, in less than about 0.1 second for high performance positioning means and in less than about 1 second for ordinary positioning means. A custom designed system would allow the ejector to be moved from one reservoir to another, with repeatable and controlled acoustic coupling, in less than about 0.001 second.

In order to provide a custom designed system, it is important to keep in mind that there are two basic kinds of motion: pulse and continuous. Pulse motion involves the discrete steps of moving an ejector into position, emitting acoustic energy, and moving the ejector to the next position; again, using a high performance positioning means with such a method allows for repeatable and controlled acoustic coupling at each reservoir in less than 0.1 second. A continuous motion design, on the other hand, moves the ejector and the reservoirs continuously, although not at the same speed, and provides for ejection while these movements are occurring. Since the pulse width is very short, this type of process enables reservoir transitions to occur at a rate of more than 10 Hz, and even at more than 1000 Hz.

In order to ensure the accuracy of fluid ejection, it is important to determine the location and the orientation of the fluid surface from which a droplet is to be ejected with respect to the ejector. Otherwise, ejected droplets may be improperly sized or travel in an improper trajectory. Thus, another embodiment of the invention relates to a method for determining the height of a fluid surface and the proximity of a cell in a reservoir between ejection events. The method involves acoustically coupling a fluid-containing reservoir to an acoustic radiation generator, and then activating the generator to produce a detection acoustic wave that travels to the fluid surface and is reflected therefrom as a reflected acoustic wave. Parameters of the reflected acoustic radiation are then analyzed in order to assess the spatial relationship between the acoustic radiation generator and the fluid surface. Such an analysis will involve the determination of the distance between the acoustic radiation generator and the fluid surface and/or the orientation of the fluid surface in relationship to the acoustic radiation generator.

More particularly, the acoustic radiation generator may be activated so as to generate low energy acoustic radiation that is insufficiently energetic to eject a droplet from the fluid surface. This is typically done by using an extremely short pulse (on the order of tens of nanoseconds) relative to that normally required for droplet ejection (on the order of microseconds). By determining the time it takes for the acoustic radiation to be reflected by the fluid surface back to the acoustic radiation generator, and then correlating that time with the speed of sound in the fluid, the distance—and thus the fluid height—may be calculated. The presence and depth of a cell beneath the surface can be determined likewise. Of course, care must be taken in order to ensure that acoustic radiation reflected by the interface between the reservoir base and the fluid is discounted. It will be appreciated by those of ordinary skill in the art that such a method employs conventional or modified sonar techniques.

Once the analysis has been performed, an ejection acoustic wave having a focal point close to the center of a cell near the fluid surface is generated in order to eject at least one droplet of the fluid, wherein the optimum intensity and directionality of the ejection acoustic wave is determined using the aforementioned analysis, optionally in combination with additional data. The "optimum" intensity and directionality are generally selected to produce droplets of consistent size and velocity. For example, the desired intensity and directionality of the ejection acoustic wave may be determined by using not only the spatial relationship assessed as above, but also: geometric data associated with the reservoir, fluid property data associated with the fluid to be ejected, cell dimensions and consequent cell volume, and/or historical cell-containing droplet ejection data associated with the ejection sequence. In addition, the data may show the need to reposition the acoustic radiation generator with respect to the fluid surface, in order to ensure that the focal point of the ejection acoustic wave is near the fluid surface, where desired. For example, if analysis reveals that the acoustic radiation generator is positioned such that the ejection acoustic wave cannot be focused near the fluid surface, the acoustic radiation generator is repositioned using vertical, horizontal, and/or rotational movement to allow appropriate focusing of the ejection acoustic wave.

Because one aspect of the invention is ejection of a single cell, the selective nature of the invention will be immediately appreciated. Using simple ejection, cells of sufficiently different size can be separated, starting with ejection of the smallest cells. The device can thus be employed as a type of cell sorter, in addition to its use for making arrays. For example because monocytes (diameter 20 µm) are much larger than both small (diameter 8 µm) and medium and large lymphocytes (diameter 12-14 µm) (corresponding to a cellular volume for monocytes of about 3 times greater (large lymphocytes) to about 16 times greater (small lymphocytes)), a mixture of these cells may be selectively ejected for arraying or sorting. The minimum acoustic energy level adequate to eject small lymphocytes will be insufficient to eject the large lymphocytes and monocytes. Once all the small lymphocytes have been ejected, the large lymphocytes may be ejected using a minimum acoustic energy level adequate to eject large lymphocytes (which will be adequate for ejecting medium lymphocytes), with little danger of ejecting the much larger and heavier monocytes. Surface functionalization with cognate moieties to marker moieties displayed externally on a cell exterior offers another level of selectivity, albeit requiring ejection onto a surface. Finally, as the invention provides for acoustic location of a cell to determine whether it is close enough to the surface to be ejected, various properties may be measured and used as additional criteria for ejection. One of skill in the art of cell sorting will appreciate that such ejection with additional criteria can be adapted to traditional cell sorting applications, by ejection in a trajectory appropriate to transfer the ejected cell to another fluidic container, or by spotting onto a substrate and subsequently washing the desired cells into a container. Likewise, the invention as adapted to sorting circumscribed volumes (such as cells) that have a different acoustic impedance than the carrier fluid, is clearly adaptable to sorting particles (such as glass or polymer beads), including particles tagged with a specific moiety or particles that may be otherwise evaluated by measurement of some property. Properties useful in sorting cells, and other circumscribed volumes that differ in acoustic impedance (such as solid or gel particles), include acoustic density and size, both of which can be measured by known acoustic means. Density can be calculated from the reflection coefficient obtained by measuring the acoustic waves reflected by the interface between the circumscribed volume and the carrier fluid. Size and shape can be measured by the use of conventional sonar methods.

The instant invention embodied as a cell sorter is preferably configured with at least one channel, preferably more than one channel, from which cells are ejected. An ejection channel preferably allows cells that are to be sorted to pass in single file. Cells may be ejected to other types of containers, including fluidic channels, or onto a substrate not having partitions, such as a planar array where the cells are localized by attachment at sufficient distances from one another to form a virtual separate container for each cell; alternatively, the substrate may have some cells arrayed close enough to permit interactions between them in the virtual containers. Conventional containers, such as an array of wells on a commercial well plate, may serve as physical containers for an array of virtual containers of one or more cells, or may serve as receptacles for individual cells or for multiple cells of one or more cell type. Mixtures of cells, such as monocytes, B lymphocytes, and T lymphocytes, may be desired for a particular experiment.

Multiple ejectors for each ejection channel can increase throughput, especially with multiple channels, and this configuration is preferred. Each ejector may be coordinated with one or more sensing or detecting means. Such coordination may be effected manually, as by an individual operating the one or a plurality of ejectors associated with a given ejection channel. Preferably, the coordination of detection and ejection is accomplished by an integrated system that employs a processor, which makes the selection based upon preselected parameters for the detected property. Different ejection channels may be designed for cell populations of different sizes, which can be separated by size using conventional means, such as enrichment techniques and absolute filtration. The preferred multiple ejectors for each ejection channel may eject cells to multiple targets, such as multiple well plates or different wells in the same plate, or different containers, including fluid channels.

Target channels for carrying selectively ejected cells to a destination may be provided. For convenient ejection of cells from an ejection channel that is open on top in at least one region, into efferent or target channels (or other containers) located nearby that are also open on top, the acoustic ejection means or source of focused acoustic energy should be capable of imparting a non-vertical trajectory (i.e., a trajectory that has a velocity component parallel to the fluid surface) to the ejected droplet. It will readily be appreciated that such a non-vertical ejection velocity, if not parallel to the flow in the ejection channel, can eject a droplet into a container such as a target channel that is horizontally spaced from the ejection channel. Such a target channel for receipt of cells from an ejection channel may or may not be in fluidic contact with the ejection channel; further, the target channel for receiving an acoustically ejected cell or cells may also serve as an ejection channel for ejection of the cell to another target channel or container, including the channel from which the cell was originally ejected.

For maximum separation efficiency and flexibility, the horizontal (or surface-parallel) component of the ejection velocity may be varied to permit ejection of a cell (1) vertically from the fluid, (2) parallel to the flow of the ejection channel such that the sole non-vertical component of the velocity is imparted by that flow, or (3) with various non-vertical velocity components that are not parallel to the direction of fluid flow in the channel. Such directionality of ejection (controllable by the focusing of the acoustic ejector itself) permits, for example, the ejection from a central ejection channel by a single ejector to either of two target channels flowing on either side of the ejection channel, each target channel flowing in substantially the parallel or anti-parallel direction to the flow of the ejection channel. Most preferably, such an adjustable acoustic ejector may be moved to eject cells from one channel to another. For example, in the three-parallel-channel arrangement where cells are ejected to one or the other lateral channels from a central channel, the ejector may be preferably moved to either lateral channel to eject cells, either back into the central channel, to the opposite laterally spaced channel from the central channel, or to other channels than the three described above, that are sufficiently near the lateral channels.

Additionally, it will be readily appreciated that, during ejection, the fluid in the ejection container or channel, or in the target container or channel, need not flow in any specific direction, or at all, either absolutely or relative to the fluids in other containers or channels. In cases of fluid flow, the target channels may loop towards the ejection channel, or the ejection channel may loop towards a target channel; alternatively, the target or ejection channels may cross over or under each other, as may be conveniently fabricated by routine microfabrication methods (see, for example, U.S. Pat. No. 6,044,981 to Chu et al., teaching of a nanometer-scale buried channel filter constructed using sacrificial oxide and standard photolithographic techniques that employ the layering of a silicon material).

For clinical cell sorting applications, where speed and high throughput may be desired for medical reasons, limited sorting is often possible. For example, only certain specific cells, such as immature stem cells, need to be separated for infusion in the case of heterologous allografts (or possibly xenografts). For autologous reinfusion, only diseased cells need to be removed. In such cases, the multiple acoustic cell ejection means "pre channel" may be used to eject the undesired cells from a given channel sequentially or in series, as coordinated with the single or plurality of detecting means to increase the cell throughput per channel. This increased throughput per channel is in addition to that achieved by using a combination of multiple channels for simultaneous ejection.

Figure 7A:
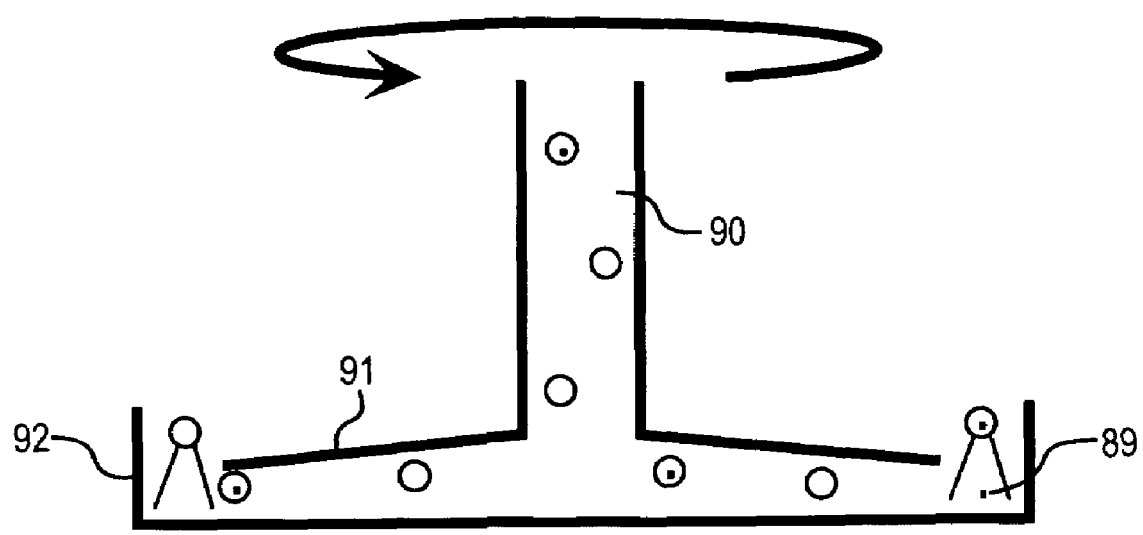
FIGS. 7A and 7B, collectively referred to as FIG. 7, depict a device having a central fluidic channel that feeds cells, at a high rate, laterally to a peripheral channel from which the cells are ejected onto the substrate, preferably by the use of multiple ejectors.
Figure 7B:
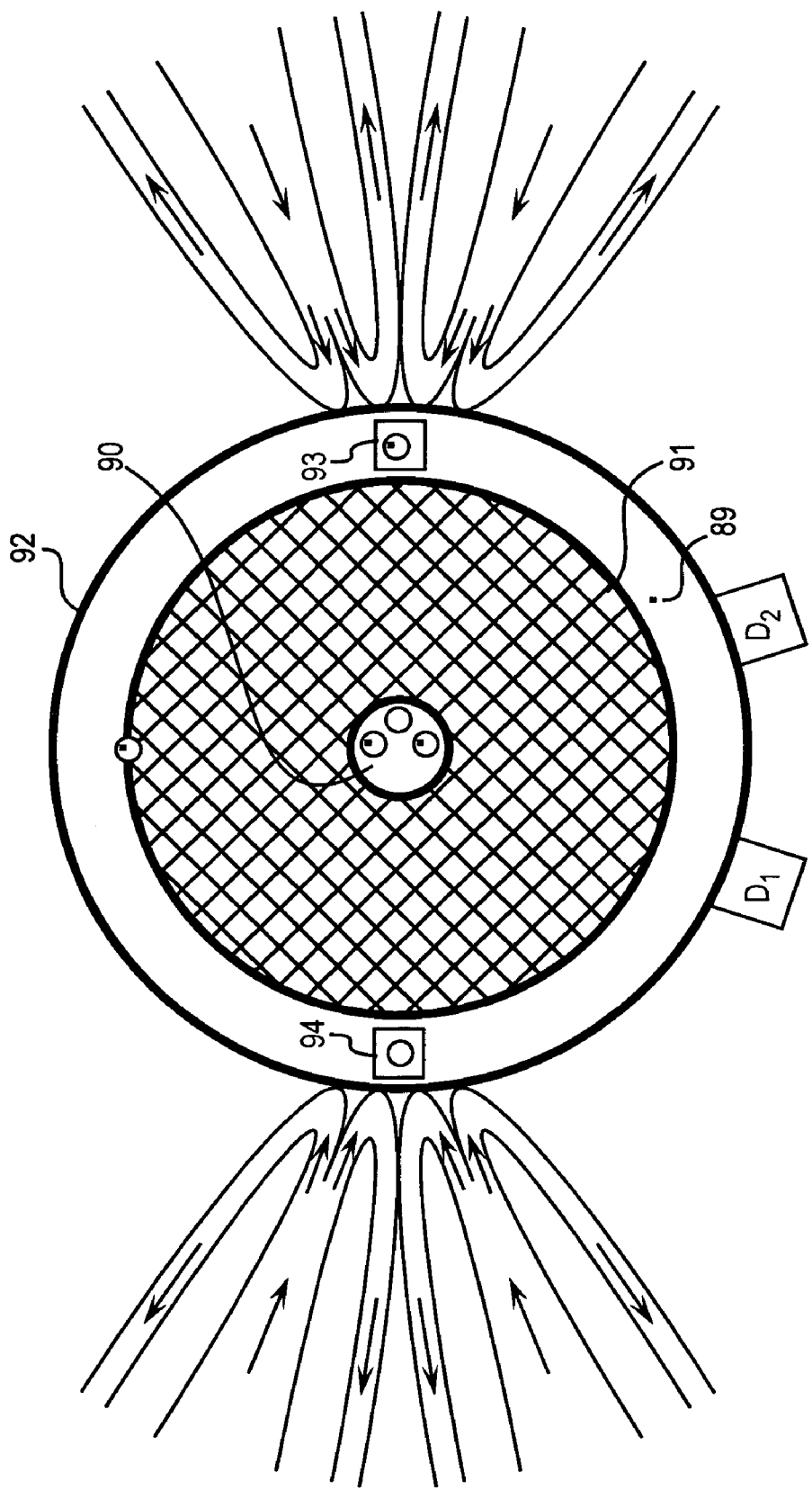

FIG. 7 depicts a device having a central fluidic channel that feeds cells, at a high rate, laterally to a peripheral channel from which the cells are ejected onto the substrate, preferably by the use of multiple ejectors. FIG. 7A illustrates a side view of a vertical channel containing cells, within a larger vessel. Fluid from the vertical channel is only accessible to the periphery of the larger vessel by passing under an angled lip projecting laterally from the vertical channel, with the distance between the lip and the floor of the larger vessel decreasing radially outward so that cells can pass radially outwards from the central channel to the periphery. At the periphery, a channel is formed where cells are spaced further apart relative to their spacing in the vertical channel, and they move in the horizontal plane. FIGS. 7A and 7B depict two focused acoustic elements at two ejection sites 93 and 94, located at the outer circumference of the rotating fluid chamber for ejecting cells, that reach a peripheral channel 89, located just inside the container wall 92. A collecting device or substrate is not shown. Multiple focused acoustic elements are preferably placed on the circumference, with each preferably preceded by at least one cell property detector, here $D_1$ and $D_2$. Liquid can also be drawn from above the angled lip 91 to further induce particle flow to the ejection zone at the focal spot of the acoustic element, and to decrease the horizontal area in which a cell may be present. This configuration has the advantage of sweeping a large volume of fluid into the ejection zone and increasing both throughput and overall efficiency of cell sorting. The entire volume of fluid, and all contained cells, pass through a common central channel 90 prior to passing under angled lip 91 en route to the peripheral channel 89. Excess fluid entering the peripheral channel 89 may be removed by acoustic ejection (not shown), or by conventional microfluidic channels having a dimensions too small for the cells that are separated to pass through; such channels will be appreciated as readily made by routine microfabrication techniques.

In addition to multiplexing detectors and ejectors in one such separation unit, multiple such units may be simultaneously employed in parallel to greatly enhance throughput and efficiency. Furthermore, non-binary ejection decisions may be made at each ejector in the unit, and further flexibility may be obtained by employing units in series for complex separations. Units employed in series may be optimized for successively different mean cell sizes or other cell parameters for complex sorting procedures.

The preferred directable acoustic ejection means can be adjusted to vertically eject a droplet, despite fluid motion, by ejecting the droplet with a horizontal velocity exactly equal and in an opposite direction to the fluid flow in the channel. The ejection means can as easily be adjusted to eject the droplet with a net horizontal velocity in a direction perpendicular to the fluid flow in the channel, whether or not there is any horizontal velocity relative to a stationary frame of reference parallel to the fluid flow of the channel. Thus, for example, a droplet containing a cell may be ejected from one directable ejector to one of two channels near the ejection channel, or onto a substrate surface disposed above the ejection channel. The ejection is non-binary because four choices exist: not ejecting, ejecting to each of two possible channels, and ejecting to the substrate surface. Similarly, even without the solid substrate as a possible target for ejection, the choices of not ejecting or ejecting to either of the two target channels provide a ternary rather than binary selection scheme at a single ejector.

Various detection means are routinely employed, often using tags such as specific antibodies (Abs) that are imparted with some property, such as being ferromagnetic or fluorescent or the like. Such tagged and intrinsic properties, such as intrinsic fluorescent properties, can be used to determine cellular characteristics such as diameter, the ratio of nuclear volume to cytoplasmic volume, and, in some cases, intra-cytoplasmic and intranuclear conditions. For example, measuring intrinsic fluorescence of the amino acid tryptophan (Trp) can yield valuable information as to a cell's identity by detecting contributions to the net spectrum from specific proteins, or of the same proteins under different conditions. Each tryptophan molecule will have absorption and emission spectra that are affected or shifted by the local environment of the molecule. Thus one protease will have a different spectrum than another protease, and the same protease will experience a shift in its spectrum if the pH of the fluid surrounding it is changed. Thus among granulocytes, for example, the neutrophils or polymorphonuclear cells (PMNs), with their plethora of neutrophilic membrane-surrounded granules, will exhibit a different net intrinsic Trp fluorescence than eosinophils and basophils, with their characteristically different granules. Similarly, nuclei, with high levels of densely packed histones in the chromatin, will be discernable from cytoplasm by intrinsic Trp fluorescence. Fluorescent tagging of a cell's external surface permits sizing of the cell by measuring the fluorescence emission of the cell as it flows past a detector, with the duration of emission of any components of the emission spectrum through the detection window being proportional to the dimension in the cross-section parallel to the flow. The signal is proportional to cell diameter if the longest possible duration of signal is obtained, e.g., it is obtained from across the cell center or along the longest transecting distance of the cross-section. If the detection is also of emission from all points in the cross-sectional dimension orthogonal to both the flow direction and the axis from the detector to the cell center, then the integrated intensity of fluorescence over time will yield a signal proportional to the presented cross-sectional area. Differentiation of the intensity measured as a function of time with respect to time (which in turn corresponds to distance for constant velocity flow) yields some information on geometry, with spherical cells expected to exhibit a less spiked signal than, say, cubic cells. If intrinsic fluorescence of cell contents is measured, the duration of emission is proportional to the cell diameter, while the emission intensity integrated over time is proportional to total volume passing by the detection window, and intensity differentiated with respect to time yields information on geometry.

It will be readily appreciated that any one of a number of different properties or parameters may be detected. Commonly, the detected property will require a probing or excitation signal. For example, most spectroscopic methods, including fluorescence, use measurements of electromagnetic emission or absorption that result from excitation by electromagnetic waves. Acoustic or sonar type detection require a probing signal of focused acoustic energy that is reflected as a result of differences in acoustic impedance at an interface, such as the interface between a cell surface and a carrier fluid, or the interface between the nucleus and cytoplasm. It will be appreciated, for example, that the differences in acoustic impedance between densely packed and tightly held nuclear material and looser, less dense cytoplasm permits the acoustic detection of nuclei and the determination of nuclear and cytoplasmic volumes. A good example of now-routine methods for sizing surface-fluorescent tagged cells, which employ a laser beam having a diameter larger than the largest of the cells in a mixture of cells, and in which both light scatter and fluorescence are measured, is described in U.S. Pat. No. 4,765,737 to Harris et al. It is readily appreciated that equivalent information may be derived from acoustic detection or sonar methods. The adaptability, however, of intrinsic fluorescence detection to measure nuclear and cytoplasmic volumes is appreciated to offer more reliable estimates of total cell volume, cytoplasmic volume, and nuclear volume than those values estimated from acoustic dimensional measurements. Further, as previously discussed, intrinsic fluorescence can, for example, distinguish between morphologically similar granulocytes.

The detected differences in physical characteristics may be manifested as differences in visual characteristics. These visual characteristics may be detectable by the naked eye, by microscopic examination, or by a video camera integrated with suitably programmed image processing equipment. Differences in optical characteristics, such as transmissivity, reflectivity, color, polarization, or the like, may be measured.

The differences detected may be of other physical characteristics, such as electrical conductivity, capacitance, inductance, permeability to microwaves, or magnetic properties. These differences may be detected by the use of ultrasound or other acoustic energy, or by spectroscopic techniques, as long as the method of detection does not substantially affect cell viability.

Once separated according to a specific property, the cells can be further separated. For example, a mixture of cells having a wide size distribution may be separated into three size bins: large, medium, and small. These sized populations, for example the medium sized population, may each be separated again by size into three more bins. Commonly, the successive detection of smaller differences in the same property may be effected by changing detection conditions. For example, subgroups of cells separated by gross differences in size while in a rapidly moving fluid, using sonar or acoustic imaging, may be separated further by size in more slowly moving fluids. Blood cells are one example of cells that may be thus sorted. A mixture of monocytes (spheres about 11-20 µm in diameter), lymphocytes (spheres about 8 [small], 12 [medium], or 14 [large] µm in diameter), and erythrocytes (doughnutlike discs about 7 µm in diameter by about 3 µm high) may be separated by cell type through the use of an ejection channel abotu 22 µm wide. This channel employs means for reliably floating all cells, such as an appropriate-density carrier fluid that does not affect cell viability, or a physical ramp-like structure in the ejection channel just upstream from the ejection site. Lymphocytes and monocytes are ejected into appropriately sized channels, with the target channel for lymphocytes having a width of about 15 µm and the target channel for the monocytes having a width of up to about 22 µm. Some erythrocytes may be ejected with lymphocytes, and are less likely to be ejected with monocytes, because of their ability to be positioned alongside the ejected cell during ejection in the ejection channel. The lymphocytes that once flowed in the 15 µm wide channel may be sized acoustically again, using a slower rate of flow that is adequately rapid for maintaining overall high throughput, because the subpopulation of lymphocytes is merely a fraction of the total number of cells.

Alternatively, different cells in a mixture can be separated by intrinsic fluorescence using excitation at a given wavelength and measured emission per measured volume; the initially separated groups may be further separated by measuring emission at a different wavelength, which could probe a different property of the cells.

The preceding is a type of serial multiplexing, wherein different properties are measured for all or some of the initially separated subpopulations to further separate them. This method is also similar to analog separation, as selection may be made based upon the value of a continuously varying property (such as size). The method, as any form of serial processing, may be carried out in parallel to increase throughput.

For complex mixtures of cells, both serial and parallel multiplexing is preferably combined with multiple detectors and different types of detectors. For example, acoustic detection combined with intrinsic fluorescence at multiple detection sites may be used. Many parameters may be determined from measuring both acoustic reflection and fluorescence over time. For example, cellular and nuclear diameters, the presence of a nucleus, and nuclear/cytoplasmic/total cell volumes may be determined by integrating acoustic and intrinsic fluorescence data. (For the purposes described herein, the cytoplasmic volume is taken to include the volume of included organelles, such as mitochondria in macrophages and the granules of granulocytes, although these volumes are technically not cytoplasmic, and a more precise term would be extranuclear volume, i.e., total cell volume minus nuclear volume). Measuring intrinsic fluorescence emissions at various frequencies (e.g., Trp emission frequency intensity maximum for the mean over cell types in blood; that for the analogous mean of nuclei of nucleated blood cells; the frequency shift corresponding to PMN Trp emission frequency intensity maximum) will allow the selection of cells such as granulocytes that can not be distinguished by geometric parameters such as the nuclear to cytoplasmic volume ratio. Although avoiding introduced tags will usually be desirable, any selection methods involving deliberately tagged cells can also be employed with the instant invention.

Figure 6:
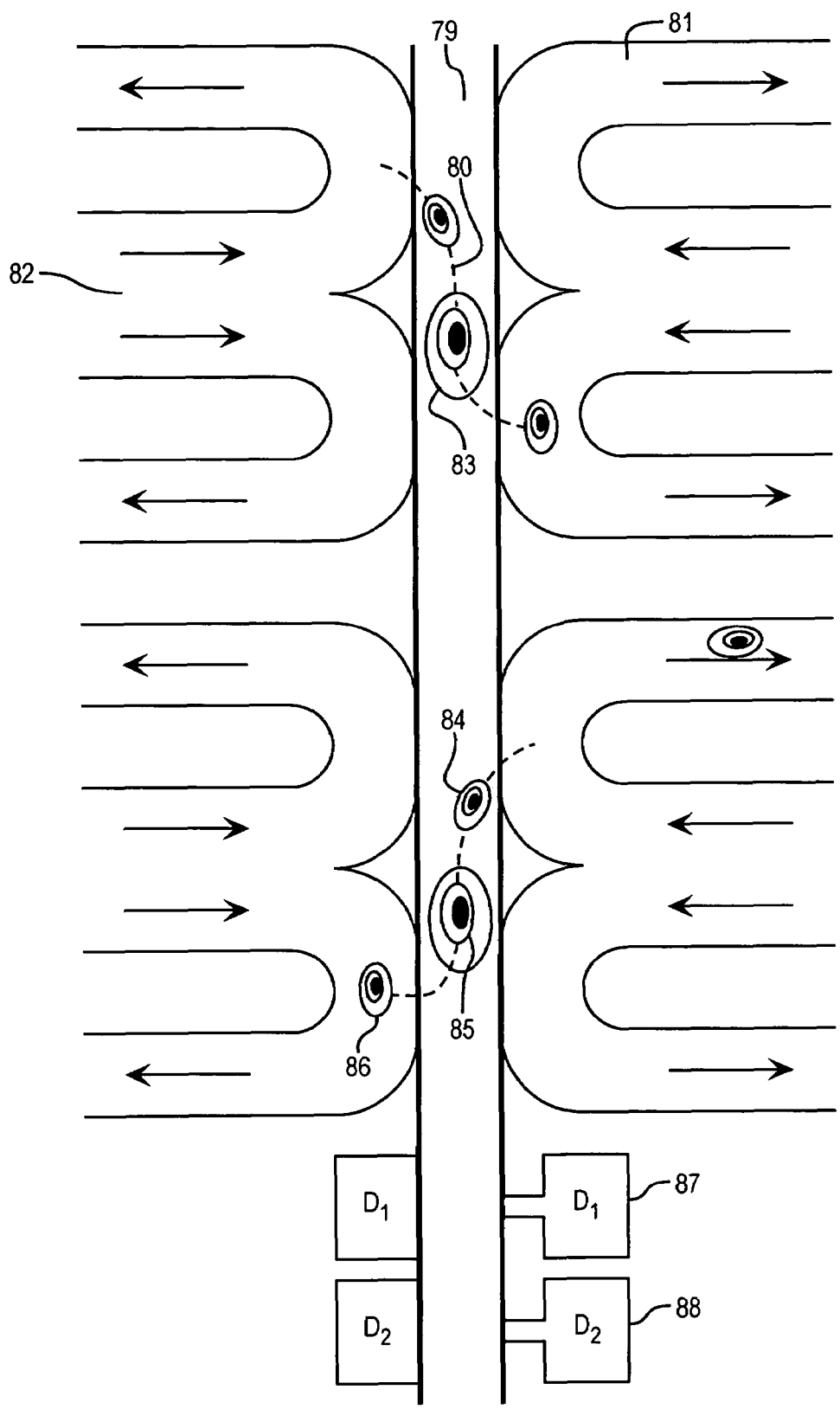
FIG. 6 depicts a top view of a central channel, an ejection channel, and two detection devices $D_1$ and $D_2$ past which cells flow. Also depicted are two ejection sites represented by large ellipses, each containing a depiction of a cell, from which cells may be ejected perpendicular to the surface onto a substrate (not shown), or into adjacent target channels.

FIG. 6 depicts a top view of a central channel, an ejection channel, two detecting devices $D_1$ and $D_2$ past which cells flow, and two ejection sites represented by large ellipses, each containing a depiction of a cell, from which cells may be ejected perpendicular to the surface onto a substrate (not shown), or into adjacent target channels. Cells flow past the detectors prior to reaching the ejection sites. Cells may be ejected from the ejection sites with the only velocity component being perpendicular to the plane substantially parallel to the fluid surface (here a horizontal plane, with the perpendicular thereto being vertical). When the perpendicular ejection velocity component is the only non-zero component of velocity, the ejection trajectory is perpendicular to the fluid surface (here vertical), permitting ejection onto a substrate surface (not shown here) for array formation as depicted in the preceding figures. Cell-containing droplets may also be ejected with a non-perpendicular velocity component, permitting trajectories such as those depicted by the dashed lines.

Channels depicted near the central or ejection channel are target channels for receiving ejected cells. At each side of the ejection site in the ejection channel, a common fluidic channel is divided into two channels just prior to reaching the ejection channel, and the two channels loop towards the ejection channel, flowing parallel and antiparallel to the fluid flow in the ejection channel for a short distance. The target channels are sufficiently close to the central channel to permit a cell to be ejected from the ejection channel to any selected target channel abutting the ejection channel near the ejection site. As configured in this depiction, a cell at one of the ejection sites may be selected not to be ejected, selected to be vertically ejected to a substrate surface (as to an array site on the substrate surface), or selectively ejected to any of the four ejection sites. There are therefore six possible ejection destinations from each site, including non-ejection, permitting up to 11 different cell subpopulations to be sorted (9 channels plus two substrate surfaces). Alternatively, the channels may be used to sort nine different types of cells or cell subpopulations, and the vertical ejection of some of these cells onto array sites on a substrate surface, such as well plate wells, may be performed simultaneously for characterization of the sorted cells.

One common task of cell selection involves colony sampling, in which agar surfaces are "stabbed" with bacterial cells or cells from other microorganisms. Typically, colony sampling devices contain an optical system that drives a robotic arm containing an inoculation loop or needle. The optical system locates a colony of interest, and the needle stabs the agar and delivers the colony to a container for further growth. These systems are sometimes unreliable in their ability to find a colony of interest.

The needles of these devices must be rinsed and sterilized between inoculations. The process of rinsing and sterilization leads to the deposition of carbon deposits and chemical residue, which can interfere with further growth of the organism of interest. Mechanical robotic arms are also prone to failure and are capable of relatively imprecise positioning for sampling closely spaced colonies or delivering cells into dense arrays.

Acoustic ejection of cells directly from colonies offers a superior method for ejection of a specific number of cells from any number of colonies of bacteria growing on an agar or other semisolid, gel, or the like. Densely packed colonies can be individually sampled without contamination of a sampled colony by cells from nearby colonies, due to the ability to precisely and accurately focus the acoustic energy.

The presence of colonies may be detected by acoustic microscopic means, e.g. by detecting a different acoustic impedance at the agar surface in a region having a colony, compared to a region having no colony. The ability to interchange or add myriad other detection means, including standard optical microscopy and detection of intrinsic tryptophan fluorescence, will immediately be evident.

Cells may be ejected into the wells of well plates or other physical containers. Alternatively, a planar substrate with or without specific means for attaching cells to the substrate may be employed. The containers or wells may contain nutritive media, for example nutritive agar, prior to ejection of cells thereon, or nutrients may be added after ejection. Adjusting the power of the acoustic energy delivered in a unit time (to a focal point sufficiently near the surface for ejection to occur, and holding this distance constant), and consequently droplet volume, permits deposition of a desired number of cells per target container or receptacle in a reproducible manner. Where multiple discrete colonies are detectible on one or more culture containers, cell samples may be arrayed by colony onto a well plate or other substrate surface.

Depending upon the organism and morphology of the colony, the cells may be ejected from the agar or other nutritive surface without the need to create specific conditions to facilitate ejection, such as reducing the viscosity of the fluid in the colony or of the underlying gel or semisolid forming the substrate or medium. Some circumstances will require means for promoting specific conditions that permit ejection. Various means for creating ejection-permissive conditions include deposition of chemical or biochemical reagents at the colony sites to affect intracellular adhesion and/or the viscosity of the extracellular fluid or the underlying agar (or other gel-like medium). For example, a fluid containing agarose (or another agar-degrading enzyme) may be deposited to liquefy the agar underlying a colony, or to reduce the viscosity of a liquid medium in order to facilitate ejection of cells from the colony. Other enzymes, for example, may be employed, depending upon the type of medium upon which the cells are grown.

Although eukaryotic cells are not typically grown on gel-like media, they will often require some treatment to reduce intracellular adhesion, which also may be required for some prokaryotic cells. If eukaryotic cells are grown on gel or another semisolid medium, effecting a phase or viscosity change in the substrate underlying the cells by delivery of acoustic or other energy can be used in conjunction with any treatment required to reduce adhesion among cells.

Preferably, the region underlying the colony is heated to a temperature that melts ($T_m$) the agar (or other gel or semisolid medium) without affecting the viability of the cells in the overlying colony. To this effect, a low $T_m$ agar or gel-like medium may be utilized. Also, the phase change must be localized to the region underlying the colony from which cells are to be ejected so that neighboring colonies are not disrupted. Wholesale melting of all the medium in an agar plate containing numerous colonies would be undesirable because all the discrete colonies would coalesce before some cells from each could be ejected. In order that cells may be ejected from each colony in rapid succession, the localized phase change or melting of the medium underlying the colonies from which the cells are successively ejected must be achieved rapidly. Various means of rapid localized heating may be employed. For example, an electric heating element comprising a thin member or pin can be inserted under the colony and the underlying medium melted by an electrical pulse.

Heating means that do not require physical contact between the heating device and the medium are preferable. For example, directed electromagnetic energy, such as directed microwave or infrared radiation or a laser beam having an appropriate cross section and frequency, may be employed. Preferably, the source of electromagnetic radiation is located so that the electromagnetic waves must pass through the medium underlying a colony from which cells are to be ejected, e.g. the source is located under the medium, so that the underlying medium is heated earlier and to a greater extent than the cells in the overlying colony, to shield the cells from undesired heating.

Liquefying the medium beneath a colony by focused acoustic energy is a most preferable means of effecting localized melting because the depth as well as the breadth of the volume to which thermal energy is delivered can be controlled. Focused acoustic energy can be used to heat a cylindrical region having a diameter of as little as about 20 µm and height of as little as about 200 µm, without significant heating outside the cylindrical area for substances that have moderate thermal conductivity. Thus, once a colony is located, for example by acoustic means, the focus of the acoustic energy can be adjusted so that the power is insufficient to deliver the threshold energy to eject a droplet from the surface. The region of heating is spatially controlled in a plane parallel to the medium surface (breadth) to be wholly underlying the boundaries of the colony of interest. The depth of acoustic focus and of heating is adjusted to be below the surface or interface between the medium and the overlying colony, thereby further preventing ejection. To effect more uniform heating at the desired focus without ejection, the frequency of the acoustic wave may be reduced relative to the frequency used for ejection. The acoustic wave amplitude may be adjusted to adjust heating rapidity.

In some cases, the cells forming the colonies to be ejected may be transformed to liquefy the underlying medium. For example, where an agar-based gel medium is used, cells may be transformed to release agarase, an enzyme that hydrolytically liquefies the underlying agar. Analogous enzymes may be used for different media, for example cellulase can be used to hydrolyze various polysaccharide moieties. The transformation to release agarase can be done solely for facilitating ejection from an agarose gel material, or it may be done in conjunction with another transformation to selectively facilitate ejection only from colonies that have been transformed. For example, bacteria may be transformed with a construct for the expression of pancytokeratin (a mammalian protein) in the cytoplasm and for the release of agarase to the cell surroundings, so that the ejectability is a marker for the transformed cells.

Although not required for the methods and systems for sorting and arraying cells of the instant invention, the preferred serial and parallel multiplexing of detection and ejection lend themselves to, and are preferably integrated with, a processor. The processor functions to integrate the various detection data and to calculate the time that a detected and measured cell will arrive at an ejection site, and to effect the appropriate ejection, rendering the ejected droplet-contained cell with the appropriate velocity vector and trajectory to correctly target the target container, channel, or array site. Maximum efficiency and throughput can be thus effected with a high level of both serial and parallel multiplexing of detection and ejection sites, with a large number of selectable ejection targets at each site.

The ability to measure a property as an ejection criterion, in addition to permitting the invention to be used for cell sorting, permits the sorting of non-living solids, gels, and fluid regions discrete from the carrier fluid. It will be readily appreciated that the ejection of; for example, beads used for solid phase combinatorial synthesis and bearing some marker or property identifying the combinatorial sequence, may be separated by the method of the invention.

EXAMPLE 1

Acoustic Ejection of Monocytes onto a Substrate as an Array from A Mixture of Cells from Peripheral Blood with Concurrent Separation of Red Blood Cells, Granulocytes, and Lymphocytes into Channels Rabbit polyclonal-Ab against human MHC (displayed on all cells) is generated and a single clone is selected that binds an MHC epitope common to all humans rather than to the epitopes specific to individuals. A substrate is functionalized with the monoclonal antibody (mAb) by routine methods. Monocrystalline Si is chosen as the substrate because of the plethora of known methods for functionalizing Si.

A channel having a width of 25 µm, as illustrated in FIG. 6, is utilized to reduce the time spent searching for cells to eject. This central ejection channel component of the sorting unit is about 6 cm in length, open on top between about 2.75 and 3.25 cm and at one end for about 0.5 cm. The blood cells are supplied from fluidically connected channels, not shown. Two detectors, $D_1$ and $D_2$, are deployed at about the first 0.5 cm of the depicted channel. The focused acoustic energy transducers are located directly beneath ejection sites in the regions of the ejection channel that are open on top. To each side of each ejection site, a common fluidic channel divides into two channels that loop towards the ejection channel such that, for a short distance, fluid in one channel flows parallel and fluid in the other antiparallel to the fluid flow in the ejection channel; these two channels are sufficiently close to the ejection channel to permit a cell to be ejected from the ejection channel to a selected target channel. There are four target channels per ejection site, and eight in all. The acoustic ejection can impart a zero-magnitude velocity component, or a non-zero directional velocity component, parallel to the fluid surface, e.g. in any horizontal direction. This permits cell-containing droplets to be acoustically ejected, based upon detected properties, to any of the four target channels or onto a substrate surface oriented substantially parallel to the fluid surface above the ejection site, or not at all. The channels are fabricated of an HF-etched glass plate heat-fused to a cover glass plate (except where open on top) by routine microfabrication techniques.

The detectors employed are laser/intrinsic fluorescence ($D_1$) and acoustic imaging ($D_2$). The acoustic ejection transducers also perform some detection functions at the ejection site, at a minimum detecting whether the cell is sufficiently close to the fluid surface for ejection. Cells are forced to the surface by a ramp-like structure, as depicted in FIG. 5D. Added stringency is effected by adjusting the acoustic energy delivered based upon the volume of the cell to be ejected, thus precluding the ejection of substantially larger cells if there is a mistake in sizing that substantially underestimates cell size.

Fluorescence, light scatter, and acoustic data are input to a processor that controls the process. Sizing data, including dimensions, volumes of cells and detected nuclei, and pertinent cytoplasmic/total/nuclear size or volume ratios, are obtained from integrated acoustic, fluorescence, and/or scattering data. The intrinsic Trp fluorescence emission spectrum is also measured for each cell. A decision tree is based on sizing and volume ratios first, and intrinsic fluorescence data second, as the majority of cells will be distinguishable by morphological characteristics. Red blood cells (RBCs) will have some overlap in their larger dimension with small lymphocytes, but will have a much smaller total volume even if the radii are identical, because lymphocytes are spherical while RBCs are doughnut shaped. RBCs will also be non-nucleated. Small lymphocytes will have large nuclear to cytoplasmic (and nuclear to total cell) volume ratios, as will medium and large lymphocytes. Medium and large lymphocytes will overlap in size with granulocytes and small monocytes, but will have substantially larger nuclear to cytoplasmic volume ratios than either, making employment of fluorescence spectrum data unnecessary, except for added stringency, in most cases. Monocytes that overlap in size with granulocytes will tend to have different morphological characteristics, including a larger nuclear to cytoplasmic volume ratio and a continuous nuclear signal, with their two-lobed nucleus appearing almost spherical; granulocytes will have a discontinuous nuclear signal and will thus appear to be multinucleate because of their multi-lobed nuclear morphology. A fluorescence spectrum will provide the conclusive data for some small monocytes, to ascertain that they are not granulocytes or large lymphocytes. Granulocytes, including PMNs, eosinophils, and basophils, are morphologically similar and thus distinguished based upon differences in their intrinsic Trp fluorescence emission spectra, which are characteristically shifted as a result of their different characteristic granules. Platelets are also present in peripheral blood and are technically cell fragments, nonnucleated, and smaller than RBCs. Because they are of use in surgical procedures, they are not ejected from the central or ejection channel and are collected for further purification with the blood plasma.

The peripheral blood separated may be from an individual or from a number of individuals, although, as will be readily appreciated, Igs must be removed from the blood before mixing different antigenic blood types. The eight target channels at the two ejection sites are used for the different ejected cells, with small, medium and large lymphocytes, and excess monocytes ejected from the most distal ejection site, ejected to separate ejection channels. At the ejection site proximal to $D_1$ and $D_2$, PMNs, eosinophils, basophils, and RBCs are ejected to separate target channels. The proximal site is also used to create an array of monocytes for experimentation, using the substrate provided. It will be readily appreciated that an additional array of one or more cell types may be simultaneously made at the distal ejection site; for example, an array may be created of all the nucleated cell types where no nearest neighbor is of the same cell type, or an array may be created of large lymphocytes, which are more likely to be memory lymphocytes. The ejection channel is fluidically connected by routine methods to a fluid column to which a cell suspension is added. The dimensions of the column allow 5 mL of fluid carrier and cells to be added, so that a sufficient column pressure exists to initiate fluid flow through the channel and to allow fluid to reach the open-top area in a sufficiently short time. Next, the top of the column is connected to a pressure regulator that allows the gas pressure above the carrier fluid in the column to be regulated to permit fine adjustment, termination, and reinitiation of carrier fluid flow through the channel.

The carrier fluid may be a physiologic saline or other electrolyte solution having an osmolality about equivalent to that of blood serum. The monocytes are spotted onto a substrate maintained at about 38° C. The substrate employed is planar, and a density of 10,000 sites/cm$^2$ is chosen, with each site occupied by a single cell. Circulating monocytes from 10 different individuals are obtained and purified by routine methods.

The monocytes of each individual are attached to the array by acoustic ejection of a droplet having a volume of about 4.2 pL. Specifically, every tenth site of each row of the array is spotted with monocytes from one individual, and the deposition of that individual's cells is staggered in subsequent rows to increase the separation between cells from an individual. Separation of an individual's cells is preferable because it provides an internal control against variation in conditions among different substrate areas. The monocytes from the remaining individuals are similarly spotted onto the array sites in acoustically ejected droplets. Ten duplicate arrays are made.

Because monocytes are attracted by chemotaxis into inflamed tissues (where they are transformed into macrophages under the influence of immune mediators), the arrays are studied by immersing them in various physiologic solutions containing one or more inflammatory mediators, such as histamine, interleukins (ILs), granulocyte macrophage colony stimulating factor (GM-CSF), leukotrienes, and other inflammatory mediators known in the art. The cells can also be exposed to other conditions that might affect inflammation, such as heat and known anti-inflammatory agents, including steroids, non-steroidal anti-inflammatory drugs, and other substances suspected to affect the activation of macrophages. It will be readily appreciated that certain mediators and combinations thereof will have a pro- or anti-inflammatory effect, and that there will be differences among individuals and to a lesser extent among individual cells. Because the monocytes are attached by the mAb/MHC specific attachment, the array will not be disrupted by immersion.

The transformation of the monocytes into macrophages and of macrophages back to monocytes may be observed by light microscopy without affecting cell viability Other known methods of measurement of individual cells include XPS (X-ray photoelectron spectroscopy) of individual cells. Because immune cells, especially activated macrophages, are able to activate other immune cells by release of immune mediators and chemotactic agents, the possibility exists that one individual's monocytes may be unresponsive to an immune mediator or condition, but responsive to the immune mediators released by another individual's macrophage that was responsive to the experimental conditions. To control for the preceding, standard well plates are employed as controls using the identical method, with multiple monocytes from the same individual in each well (for 96 well plates, 9 wells/individual, 110 cells each). A final control, using well plates without the mAb/MHC attachment system, is also created by the method described, with surface tension sufficing to hold the ejected cell-containing droplets in place. It is readily appreciated that the 110 droplets deposited in each well plate are preferably deposited at different locations within the well to prevent the formation, by multiple deposition, of droplets too big to be held in place by surface tension.

The high throughput design depicted in FIGS. 7A and 7B, and described in the foregoing, may also be employed in substantially the same manner as used in this example with the configuration depicted in FIG. 6. One advantage of this design is that the cells are inherently recirculated. In some instances an ejection site might be overwhelmed by the number of cells that must be manipulated. In the case of blood, this situation is especially applicable to RBCs, which are the most numerous cells. The ability to overcome this problem by using more than one ejector for the ejection of the RBCs, or adding a third RBC-dedicated ejector to the system (as embodied in the systems illustrated in FIGS. 6 and 7), will be readily apprehended. Recirculating RBCs that are not ejected in a first pass (in order to permit the orderly procession of cells without disruption of flow) can be ejected later by recirculating the carrier fluid after all the less numerous cell types have been sorted. The embodiment depicted in FIGS. 7A and 7B is especially suited for such recirculation.

EXAMPLE 2

Bronchoalveolar Lavage Human Airway Epithelium (HAE) Cell Array for Studying Inflammatory Response with Simultaneous Cell Counting The method of the preceding example is adapted to arraying HAE cells obtained from bronchoalveolar lavage with simultaneous sorting and differential cell counting. In addition to epithelial cells, bronchoalveolar lavage fluid routinely contains other cells. Cells found in lavage fluid include the agranulocytic leukocytes, lymphocytes, and monocytes, which are typically activated as macrophages, and granulocytic leukocytes, neutrophils (PMNs), eosinophils, and basophils. Often present are pathogens such as viruses, including influenza viruses and DNA viruses, including herpesvirus family members, most notably CMV (cytomegalovirus) and KSV (Kaposi sarcoma associated herpesvirus); fungal species, including *Cryptococcus albidus, Coccidioides immitis*, and *Aspergillus flavus;* eukaryotic opportunistic pathogens such as *Pneumocystis carinii*, which is found in healthy patients and causes pneumonia in the severely immunocompromised; members of gram positive and negative bacteria groups; mycobacteria species; and obligate intracellular prokaryotes, such as chlamydia, mycoplasma, and rickettsia. With the possible exception of the obligate intracellular prokaryotes, all the pathogens may be cultured by routine microbiological and virological methods from the fluid remaining after all mammalian cells have been ejected. *Pneumocystis carinii* cysts (diameter 5-7 µm), trophozoites, and sporozoites may be ejected for staining, as may extracellular bacteria (typical diameter 1 µm). Staining and examination may be done instead of or in addition to culturing, as required for identification. *Pneumocystis carinii* cysts, for example, are identifiable without culturing by microscopic examination of stained specimens.

The sorting, counting, and arraying proceeds substantially as described in Example 1, with the additional recording of the identity of each cell ejected for counting purposes. Commonly, differential counts alone will provide useful diagnostic and pathophysiologic information. For example, elevated eosinophils and lymphocytes will indicate asthma or related eosinophilic lung inflammatory processes. Separated lymphocytes may be further ascertained to have elevated activated T lymphocytes expressing cell surface activation markers HLA-DR, IL-2R (interleukin 2 receptor) and VLA-1. Alternatively, the lymphocytes can be arrayed onto a substrate functionalized at different sites with antibodies that recognize the markers just mentioned. Fibrotic inflammatory disease of the lower airways, termed generally interstitial lung disease, will produce a predominance of PMNs and alveolar macrophages. Immunocytochemistry of macrophages, and to a lesser extent PMNs and airway epithelial cells, demonstrates these cells to contain characteristic cytokines, for example IL-1β, IL-6, and IL-8, in chronic lung disease of prematurity (Kotecha et al. (1996) *Pediatric Res.* 40:250-56). Bacterial pneumonias are distinguishable because they produce similar differential cell counts, but with more immune cells and bacteria particles in the lavage fluid and sometimes within macrophages.

Using the differential cell counts and microbiological/virological pathogen culture and identification methods, eosinophilic and neutrophilic primary inflammatory processes are distinguished from one another and from inflammations secondary to infectious processes in the patients from which lung lavage samples are taken. HAE cells from the patients are also studied in the arrays.

As is readily appreciated, a channel having appropriate dimensions must be provided (Oust larger than the HAE cells and possibly the large monocytes, thus approximately 25-30 µm). Alternatively the width of the channel is just wider than the cells; to permit faster loading, the depth is approximately three times the diameter of the cells, and a ramp (as depicted in FIG. 5D) is employed in the channel flow path just prior to the channel region, which is open. As a further option, a photon field (as may be provided by a laser as commonly used in optical tweezers) may be employed to force the cells close to the surface. Arrayed HAE cells are obtained by bronchoalveolar lavage, and ejected onto the substrate surface during sorting and counting as described herein and in the preceding examples. Before being loaded for ejection, the lavage fluids are treated to suspend adhering cells as individual cells by disaggregating them using conventional tissue culture methods.

Experiments on HAE cells may be conducted under conditions that permit cell division. The need for the preceding, as well as the conditions required for this, will be appreciated by one of ordinary skill. The controls with well plates are useful but not as critical as with the monocytes.

EXAMPLE 3

HAE Cell Array for Studying Individual Susceptibility to Mutagenesis as a Proxy for Carcinogensis The method of the preceding example is adapted to permit exposing the arrayed HAE cells to chemical and other mutagens, such as heat and radiation. Genetic damage is measured at different times after the exposure is discontinued by routine methods, for example biochemical assaying of broken crosslinks and other damage to DNA. Differences in DNA repair enzyme genetics may be studied by comparing recovery (extent of reduction of damage) at various times after exposure. The well plate arrays remain useful as controls, and cells may be cultured in the well plates, or array cells may be removed and cultured, to determine the appearance of dysplastic or neoplastic cells in subsequent cell generations after the exposure, and the extent of any dedifferentiation in any dysplastic or neoplastic cells detected.

EXAMPLE 4

Cell Patterning

The method of Examples 1 and 2 is adapted to pattern basal squamous cells. Basal squamous keratinizing epithelial cells and squamous non-keratinizing epithelial cells are patterned on a nitrocellulose substrate functionalized as in Example 1. The pattern generated emulates the vermillion border of the lip. The patterned cells on the substrate are then immersed in a suitable culture medium, and studies are performed regarding the formation of a skin/non-keratinizing junction.

EXAMPLE 5

Acoustic Ejection of Lymphocytes from Blood onto an Epitope Array

Small, medium, and large lymphocytes are ejected by the methods of the preceding examples to form a clonal epitopic array. Two parallel, adjacent channels are constructed with differing widths and are appropriately designed to force the cells near the surface. The wider channel is about 15 µm wide to accommodate medium and large lymphocytes; the narrower channel is 10 µm wide to accommodate small lymphocytes. Small lymphocytes may be separated from large and medium lymphocytes by routine methods, or by acoustic ejection. An amount of energy barely sufficient to eject small lymphocytes is applied as all the lymphocytes in the mixture pass through one common channel (15 µm wide). The energy is applied to each lymphocyte that is detected at the channel opening or aperture that forms the ejection region. The ejected lymphocytes may be ejected onto a substrate and washed into a petri dish or other container. Alternatively, the acoustic energy can be delivered to eject the droplet in a non-vertical trajectory so that the droplets land in a nearby container, such as a channel that is open on top and is sufficiently near the ejection channel.

The epitope array is a combinatorial tetrapeptide array formed from naturally occurring amino acids. Other epitopes are readily appreciated to exist both in proteins, as a result of non-primary structure, in peptidic molecules bearing haptens, and in other biomolecules such as peptidoglycans and polysaccharides. Only a small fraction of the approximately $10^{12}$ epitopes will be arrayed. Both T and B cells will bind these epitopes, by slightly different mechanisms, as will be readily appreciated. The tetrapeptide arrays can be made by various methods, for example by adaptation of solid phase peptide synthesis techniques to devices using focused acoustic ejection of reagents as described in the copending application on combinatorial chemistry described above. As $1.6 \times 10^4$ different natural tetrapeptides exist, 16 array synthesis areas, each 1 cm$^2$ and each containing 1,000 array sites, must be available for the synthesis of all the tetrapeptides and to maintain a density appropriate for allowing separation of individual cells.

Cells are spotted onto the array sites as rapidly as possible (thus the need for two channels to maintain single-file lines of cells in the channels despite the different sizes). When each of the 16,000 array sites has had a droplet ejected onto it, the arrays are washed to remove cells that do not bind the epitope at the deposition site. The arrays are imaged to determine which sites have bound a cell, and the cycle is repeated for sites not binding a cell, which are re-spotted. Immediately apprehended is that this process requires imaging of the array after washing, and must be automated. Automation of such a system is readily attainable, and invaluable information on clonal separation would be derived prior to completion of the project. Use of different types of epitopes would further extend the cataloguing.

EXAMPLE 6

Ejection of Bacteria to Select Transformed Bacteria

E. coli are transformed by routine methods to express pancytokeratin, a eukaryotic protein, by a construct that also causes expression and display of streptavidin on the cell surface. The cells are acoustically ejected onto a substrate biotinylated by routine methods, as described in the preceding Examples 1-5. The ejection channel size may be adapted to bacterial dimensions (1 μm), but this is attainable by known microfabrication methods. Transformed cells will be specifically bound to the biotin cognate moiety by the marker moiety, streptavidin. Washing the substrate will remove cells that have not been transformed, leaving only transformed cells attached to the substrate.

The ability to separate transformed from untransformed bacteria is combined with the ability to remove all blood cells from peripheral blood (Example 1) to evaluate the ability of transformed and untransformed E. coli to cause bacteremia in mice, and to compare the immune response mounted against the transformed and untransformed bacteria. The blood of inoculated mice is drawn and sorted as in Example 1, except that in addition to sorting all the different blood cells, the number of cells of each type is counted to provide information as to immune response. Baseline counts are done by routine methods prior to inoculation. After sorting and counting of blood cells according to Example 1, only bacteria, platelets, and plasma remain in the central ejection channel. Although roughly the same size and geometry as a platelet, a bacterium can be distinguished from a platelet by the presence of a nucleoid, where the bacterial chromosome is localized (which can be detected by light scattering or other means), or by intrinsic Trp fluorescence, which will differ between a platelet and a bacterium. All bacteria are counted and ejected, and the number and fraction of ejected bacteria that are transformed is determined by counting those bacteria that remain attached to the biotinylated substrate surface after it is washed.

Four groups of mice are evaluated. The first group is inoculated intravenously with a placebo of an appropriate carrier, such as buffered saline, having no bacteria and equal in volume to the inoculation volumes for the other groups. The second group is inoculated with carrier containing a known number of transformed, live E. coli. The third group is inoculated with carrier containing a known number of non-transformed, live E. coli of the same strain as the transformed bacteria. The fourth group is inoculated with carrier containing a known number of live E. coli of the same strain, the population being an equal mixture of transformed and non-transformed bacteria. Blood is drawn from the mice at regular intervals after the inoculation for one week, or until death of the mice from bacteremia. Statistical data on cell types and differential counts from all groups will provide data on individual variations of immune response within groups.

Data from the first group will primarily be used as a control for determining the spontaneous entry of bacteria (whether displaying streptavidin or not) into the blood of non-inoculated mice; all bacteria detected in the blood of mice from this group will be cultured and characterized for control purposes. Data from the second group, in addition to being a control for the fourth group, can be compared to data from the third group to study relative pathogenicity without competition from non-transformed bacteria. Additionally, data from the second group can be used to study loss of all or part of the construct, e.g. those bacteria obtained from Group Two mice after inoculation that do not display streptavidin and bind the biotinylated surface may be cultured and immunostained to determine whether they are expressing pancytokeratin, to quantify reversion for control purposes. Data from the third group can also be obtained for determining whether spontaneous transformation has occurred, and to explore the remote possibility that the streptavidin/pancytokeratin construct has (somehow) entered that population. The fourth group provides data on the ability of the transformed and untransformed strains to cause bacteremia under competitive conditions. Data from the fourth group on total bacteria per volume is compared with the other groups. Also, the relative proportions of transformed and non-transformed bacteria may be analyzed, after appropriate consideration of spontaneous infection, for loss or gain of transformation. For these purposes, transfer of the transforming construct by conjugation is not considered spontaneous. The possible addition of other groups with different inoculation proportions of transformed and non-transformed bacteria may also be desirable.

EXAMPLE 7

Ejection of Cells Directly from Colonies Growing on Agar Medium

One mode of accurate, contactless cell selection from colonies growing on agar is provided by focused acoustic energy to effect droplet ejection. The ejected droplets may contain one or more cells, and may be adjusted in volume to deposit more or fewer cells per ejection. A colony of cells is sampled from the center, in the plane parallel to the surface of the medium or substrate, to avoid contamination of the sample by organisms from neighboring colonies. The number of separate samples from an individual colony that may be thus deposited depends on colony size and sample size; at a minimum, several samples of even the smallest colonies can be ejected.

A routine throat smear is cultured on standard blood agar medium in a conventional plastic petri dish, and the culture is incubated at about 38° C. for 72 hours. After the incubation, an acoustic transducer is placed under the plastic petri dish containing the agar and bacterial colonies, and the presence or absence of colonies is detected via acoustic microscopy.

The same acoustic transducer used to locate the cells is used to propel the cell from the surface of the agar, provided that the surface has the correct viscosity. Focused acoustic energy is delivered immediately beneath the colony center at a focal point about 75 μm beneath the surface of the agar medium (the "thermal delivery acoustic pulse"). This pulse of acoustic energy has sufficient power and a sufficient duration to liquefy a cylinder of agar having dimensions in the plane parallel to the medium surface that are within the dimensions of the colony in this plane and extend in the direction perpendicular to the surface to the substrate surface, which liquefies at temperatures close to 45° C. (Gibco, Inc., now Life Technologies, Rockville Md., a division of Invitrogen). The need to calibrate the thermal delivery acoustic pulse to the composition and depth of the specific agar and to the petri dish, to melt cylindrical volumes of various diameters, will be immediately appreciated. Alternatively, a scanning laser may be used to heat the low-melting-point agar. Utilizing a low-melt agar permits surface liquefaction without significant reduction in the viability of the selected microorganisms on the agar surface. If a laser is employed, the laser placement can be coupled to the colony location determined by acoustic microscopy. The focal point of acoustic energy for ejection is at the surface of the medium. By locally heating the agar, the viscosity at the surface of the medium is reduced to allow ejection of the cells of interest directly into a well plate or other container.

Acoustic delivery of thermal energy is used to effect local melting beneath colonies prior to acoustic ejection. In this manner, each colony is sampled four times. Two duplicate arrays of cells ejected from bacterial colonies are made using standard well plates containing nutritive agar medium, with each droplet having a volume of about 0.1 to 1.0 pL. That the different wells may contain different media and nutrients will be immediately apprehended. Two additional samples each having a volume of about 1.0 to 100 pL (in multiple droplets as required) from each colony are deposited onto a clean surface and washed using saline into a flask containing nutritive fluid (or alternatively into channels containing flowing fluid that empty into containers of nutritive fluid).

The sampled cells are immediately cultured on petri dishes from the flasks, by conventional methods of cell culture. The array plates and flasks are stored chilled to slow bacterial reproduction, permitting future culturing and testing. The original culture petri dish is also stored chilled pending culture results. The culture results from the throat culture are examined by conventional microscopy and other means. Numerous gram negative and gram positive bacterial species are initially identified, as well as several yeast species, all non-pathogenic to immunocompetent adult humans. Further culturing from the flasks using nutritive agar media containing antibiotics, using routine methods for determining antibiotic resistance, reveals that different colonies of the same species of bacteria have different levels of antibiotic resistance, demonstrating that the different colonies are different strains or substrains.

The method of ejecting cells from colonies growing on agar medium may be used to selectively eject transformed cells. An indicator is used in the transforming construct along with the desired genetic transformation, here the expression of pancytokeratin. For example the construct can additionally transform the cells to secrete agarase, and the transformed colonies can be selected by detecting an altered acoustic impedance. Alternatively, transformed colonies may be selected optically if the construct is designed to cause transformed cells to co-express a marker such as a green fluorescent protein. Only green fluorescent colonies detected optically are ejected.

It is to be understood that while the invention has been described in conjunction with the preferred specific embodiments thereof, the foregoing description is intended to illustrate and not limit the scope of the invention. Other aspects, advantages, and modifications will be apparent to those skilled in the art to which the invention pertains. All patents, patent applications, journal articles, and other references cited herein are incorporated by reference in their entireties.

We claim:

1. A separation method comprising the steps:
   (a) detecting in a fluid having a surface, and containing a plurality of localized volumes, a single localized volume located sufficiently near the surface for ejection; and
   (b) ejecting the single localized volume from the fluid by use of focused electromagnetic or acoustic energy or both.

2. The method of claim 1, wherein the focused energy is focused acoustic energy.

3. The method of claim 1, wherein the focused energy is focused electromagnetic energy.

4. The method of claim 1, wherein the localized volume comprises a solid or gel particle.

5. The method of claim 1, wherein the localized volume comprises a cell.

6. The method of claim 5, wherein the localized volume comprises a living cell.

7. The method of claim 1, wherein the localized volume is ejected in a trajectory substantially perpendicular to the fluid surface.

8. The method of claim 1, wherein the localized volume is ejected with a non-zero velocity component perpendicular to the fluid surface and a non-zero velocity component parallel to the fluid surface to effect a trajectory whereby the localized volume experiences a net displacement in a direction parallel to the fluid surface.

9. The method of claim 8, wherein the trajectory is directionally controllable, so that the direction of net displacement parallel to the fluid surface is also directionally controllable.

10. The method of claim 8, wherein the non-vertical distance of travel parallel to the fluid surface is controllable by varying the focused energy.

11. The method of claim 8, wherein the vertical distance of travel parallel to the fluid surface is controllable by varying the focused energy.

12. The method of claim 11, wherein steps (a) and (b) are repeated for a plurality of fluids located in separate reservoirs.

13. The method of claim 12, wherein the fluid is contained in a fluidic channel.

14. The method of claim 13 wherein data from said detecting of (a) is input into a processor, whereby the processor directs said ejecting of (b) by reference to the measured data, programmed selection criteria, and system parameters.

15. The method of claim 1 wherein the localized volumes are circumscribed volumes comprising living cells.

* * * * *